United States Patent
Tsang et al.

(10) Patent No.: US 7,056,897 B2
(45) Date of Patent: *Jun. 6, 2006

(54) INDUCIBLE EXPRESSION VECTORS AND METHODS OF USE THEREOF

(75) Inventors: Thomas Chun-Chang Tsang, Tucson, AZ (US); Eugene W. Gerner, Tucson, AZ (US); David T. Harris, Tucson, AZ (US); Evan Hersh, Tucson, AZ (US); Farha Vasanwala, Needham, MA (US)

(73) Assignee: The Arizona Board of Regents, Tucson, AZ (US)

( * ) Notice: Subject to any disclaimer, the term of this patent is extended or adjusted under 35 U.S.C. 154(b) by 253 days.

This patent is subject to a terminal disclaimer.

(21) Appl. No.: 10/152,577

(22) Filed: May 23, 2002

(65) Prior Publication Data
US 2003/0207832 A1    Nov. 6, 2003

Related U.S. Application Data

(63) Continuation-in-part of application No. 10/108,486, filed on Mar. 29, 2002, and a continuation-in-part of application No. 09/185,243, filed on Nov. 3, 1996, now Pat. No. 6,709,858.

(60) Provisional application No. 60/292,943, filed on May 23, 2001, provisional application No. 60/279,634, filed on Mar. 29, 2001, provisional application No. 60/064,088, filed on Nov. 3, 1997.

(51) Int. Cl.
*A61K 48/00* (2006.01)
*C12N 15/85* (2006.01)
*C12N 15/86* (2006.01)

(52) U.S. Cl. .............. 514/44; 424/93.2; 435/320.1; 435/455; 435/456; 435/458

(58) Field of Classification Search ............. 435/320.1, 435/455, 456, 458; 424/93.2; 514/44
See application file for complete search history.

(56) References Cited

OTHER PUBLICATIONS

Hoffman et al., "Sequences involved in temperature and ecdysterone-induced transcription are located in spearate regions of a Drosophila melanogaster heat shock gene," Mol. Cell. Biol. 6(2): 663-673, Feb. 1986, Abstract only.*

* cited by examiner

*Primary Examiner*—Scott D. Priebe
(74) *Attorney, Agent, or Firm*—Oblon, Spivak, McClelland, Maier & Neustadt, P.C.

(57) ABSTRACT

The present invention relates to inducible gene expression constructs and methods of inducing gene expression using a combination of inducing agents.

23 Claims, 18 Drawing Sheets examples:
pC8: HSP70B:MCS; HIV1:IL2
pf12: HSP70B:TAT; HIV1:IL2
p007: HSP70B:TAT; HIV2:IL2

```
5'- GGATCCTTCCA CAGCCCCGGG GAGACCTTGC CTCTAAAGTT GCTGCTTTTG CAGCTCTGCC    60

ACAACCGCGC GTCCTCAGAG CCAGCCGGGA GGAGCTAGAA CCTTCCCCGC GTTTCTTTCA   120

GCAGCCCTGA GTCAGAGGCG GGCTGGCCTT GCAAGTAGCC CCCCAGCCTT CTTCGGTCTC   180

ACGGACCGAT CCGCCCCGAAC CTTCTCCCGG GGTCAGCGCC GCGCTGCCGCC GCCCGGCTGA   240

CTCAGCCCGG GCGGGCGGGC GGGAGGCTCT CGACTGGGCG GGAAGGTCG GGAAGGTTCG     300

CGGCGGGCGG GTCGGGGAGG TGCAAAAGGA TGAAAAGCCC GTGGACGGAG CTGAGCAGAT    360

CCGGCCGGGC TGGCGGCAGA GAAACCGCAG GGAGAGCCTC ACTGCTGAGC GCCCCTCGAC-   420

GCGGGCGGCA GCAGCCTCCG TGGCCTCCAG CATCCGACAA GAAGCTTAC-3'
```

FIG. 10

SEQUENCE LISTING

```
<160> NUMBER OF SEQ ID NOS: 1

<210> SEQ ID NO 1
<211> LENGTH: 469
<212> TYPE: DNA
<213> ORGANISM: Homo sapiens

<400> SEQUENCE: 1
ggatcctcca cagccccggg gagaccttgc ctctaaagtt gctgcttttg cagctctgcc    60
acaaccgcgc gtcctcagag ccagccggga ggagctagaa ccttccccgc gtttctttca   120
gcagccctga gtcagaggcg ggctggcctt gcaagtagcc ccccagcctt cttcggtctc   180
acggaccgat ccgcccgaac cttctcccgg ggtcagcgcc gcgctgcgcc gcccggctga   240
```

```
ctcagcccgg gcgggcgggc gggaggctct cgactgggcg ggaaggtgcg ggaaggttcg    300
cggcggcggg gtcggggagg tgcaaaagga tgaaaagccc gtggachhag ctgagcagat    360
ccggccgggc tggcggcaga gaaaccgcag ggagagcctc actgctgagc gcccctcgac    420
gcgggcggca gcagcctccg tggcctccag catccgacaa gaagcttac               469
```

INDUCIBLE EXPRESSION VECTORS AND METHODS OF USE THEREOF

CROSS-REFERENCE TO RELATED APPLICATIONS

This application is a Continuation-in-Part of U.S. Ser. No. 10/108,486 filed Mar. 29, 2002, which in turn is a Continuation-in-Part of U.S. Ser. No. 09/185,243, filed on Nov. 3, 1998, now U.S. Pat. No. 6,709,858 which in turn claims priority from U.S. Provisional Application Ser. No. 60/064,088, filed Nov. 3, 1997. This application also claims priority to U.S. Provisional Application No. 60/279,634 filed Mar. 29, 2001; and U.S. Provisional Application No. 60/292,943, filed May 23, 2001.

BACKGROUND OF THE INVENTION

1. Field of the Invention

The present invention relates to inducible gene expression constructs and methods of inducing gene expression using a combination of inducing agents.

2. Discussion of the Background

Gene therapy now is thought to be widely applicable in the treatment of a variety of cancers and a number of other diseases. Viral vectors are one method employed as a gene delivery system. A great variety of viral expression systems have been developed and assessed for their ability to transfer genes into somatic cells. In particular, retroviral and adenovirus based vector systems have been investigated extensively over a decade. Recently, adeno-associated virus (AAV) has emerged as a potential alternative to the more commonly used retroviral and adenoviral vectors. Lipid vectors including cationic lipids and liposomes also are used to deliver plasmid DNA containing therapeutic genes.

The therapeutic treatment of diseases and disorders by gene therapy involves the transfer and stable or transient insertion of new genetic information into cells. The correction of a genetic defect by re-introduction of the normal allele of a gene encoding the desired function has demonstrated that this concept is clinically feasible (Rosenberg et al., New Eng. J. Med, 323:570 (1990)). Indeed, preclinical and clinical studies covering a large range of genetic disorders currently are underway to solve basic issues dealing with gene transfer efficiency, regulation of gene expression, and potential risks of the use of viral vectors. The majority of clinical gene transfer trials that employ viral vectors perform ex vivo gene transfer into target cells which are then administered in vivo. Viral vectors also may be given in vivo but repeated administration may induce neutralizing antibody.

A major issue facing potential clinical application of gene therapy is the question of how to heterologous genes expressed in clinically significant quantities in selected tissues of the subject. Gene regulatory elements provide a potential answer to that question. Gene regulatory elements such as promoters and enhancers possess cell type specific activities and can be activated by certain induction factors via responsive elements. The use of such-regulatory elements as promoters to drive gene expression facilitates controlled and restricted expression of heterologous genes in vector constructs. For instance, heat shock promoters can be used to drive expression of a heterologous gene following heat shock.

U.S. Pat. Nos. 5,614,381, 5,646,010 and WO 89/00603, refer to driving transgene expression using heat shock at temperatures greater than 42° C. These temperatures are not practicable in human therapy as they can not be maintained for a sustained period of time without harm to the individual.

Gene therapy could be used in combination with a variety of conventional cancer therapy treatments including cytotoxic drugs and radiation therapies. It has been shown that hyperthermia enhances the cell killing effect of radiation in vitro (Harisiadis et al., Cancer, 41:2131–2142 (1978)), significantly enhances tumor response in animal tumors in vivo and improves the outcome in randomized clinical trials. However, the major problem with the use of hyperthermia treatment is that the hyperthermia system can not adequately heat large and deep tumors.

Likewise, the major therapies currently used to treat cancer include radiotherapy, chemotherapy, hyperthermia and immunotherapy. Gene therapy is emerging as a new treatment for cancer, with encouraging clinical results. With the emerging view of combinatorial therapy as an approach to cancer treatment (Feyerabend et al (1997) Anticancer Res 17:2895–2900; Otte (1988) Eur J Pediatr 32:17–30), there is a need to integrate gene therapy with conventional therapies. Most gene therapy approaches have utilized constitutive expression of therapeutic genes (e.g. co-receptors such as B7.1 and B7.2, cytokines such as IL-2 and GM-CSF) by viral promoters (e.g., cytomegalovirus and Rous sarcoma virus). An alternative method is the use of expression vectors that can be induced to express therapeutic genes by one or more of the aforementioned conventional therapies.

Thus, it would be useful to develop vectors that may be used at temperatures of 42° C. and below, systemically or locally, in conjunction with cancer therapies such as radiotherapy, chemotherapy, hyperthermia, and immunotherapy, to treat a patient such that the expression of the therapeutic gene(s) is activated preferentially in regions of the body that have been subjected to conditions which induce such expression.

SUMMARY OF THE INVENTION

The present invention provides methods for effecting the inducible expression of polynucleotides in cells.

The present invention provides a method of expressing a selected polynucleotide by providing an expression construct that can direct the expression of the selected polynucleotide of interest in a cell, and then subjecting the cell to heat and one or more of radiation, chemotherapy, and immunotherapy, so that the expression of the selected polynucleotide is activated.

In one embodiment of the present invention, the expression construct has an inducible promoter operably linked to the selected polynucleotide of interest, which inducible promoter is activated to the heat and/or other treatments applied to the cell containing the expression construct.

In another embodiment, the expression construct comprises both (i) an inducible promoter operably linked to a gene encoding a transactivating factor and (ii) a second promoter operably linked to a selected polynucleotide where the second promoter is activated by the transactivating factor expressed by the same construct and the inducible promoter is activated to the heat and/or other treatments applied to the cell containing the expression construct.

In one embodiment of the invention, the inducible promoter is a heat shock promoter, e.g., HSP70 or HSP70B; and the heat applied to the cell is from about basal temperature to about 42° C. As used herein the basal temperature of the cell is defined as the temperature at which the cell is normally found in its natural state, for example, a cell in skin of a mammal may be at temperatures as low as 33° C.

whereas a cell in the liver of an organism may be as high as 39° C. In specific embodiments, the application of hyperthermia involves raising the temperature of the cell from basal temperature, most typically 37° C. to about 42° C. or less. Alternatively, the hyperthermic conditions may range from about 38° C. to about 41° C., or from about 39° C. to about 40° C. Other heat shock promoters include, for example, HSP90, HSP60, HSP27, HSP72, HSP73, HSP25 and HSP28. The ubiquitin promoter may also be used as the heatshock inducible promoter in the expression construct. A minimal heat shock promoter derived from HSP70 and comprising the first approximately 400 bp of the HSP70B promoter may also be used in the invention.

In an alternative embodiment, the inducible promoter comprises a hypoxia-responsive element (HRE). This hypoxia-responsive element may optionally contain at least one binding site for hypoxia-inducible factor-1 (HIF-1).

In one embodiment of the invention; the second promoter may be selected from the group consisting of an human immunodeficiency virus-1 (HIV-1) promoter and a human immunodeficiency virus-2 (HIV-2) promoter. In preferred embodiments, the transactivating factor may be a transactivator of transcription (TAT).

The selected polynucleotide may code for a protein or a polypeptide. For instance, the selected polynucleotide may encode any one of the following proteins: ornithine decarboxylase antizyme protein, p53, p16, neu, interleukin-1 (IL 1), interleukin-2 (IL2), interleukin-4 (IL4), interleukin-7 (IL7), interleukin-12 (IL 12), interleukin-15 (IL 15), FLT-3 ligand, granulocyte-macrophage stimulating factor (GM-CSF), granulocyte-colony stimulating factor (G-CSF), gamma-interferon (IFN γ), alpha-interferon (IFNa), tumor necrosis factor (TNF), herpes simplex virus thymidine kinase (HSV TK), I-CAM 1, human leukocyte antigen-B7 (HLA-B7), or tissue inhibitor of metalloproteinases (TIMP-3). In such an embodiment, the selected polynucleotide is positioned in a sense orientation with respect to the second promoter.

Alternatively, expression of the selected polynucleotide may involve transcription but not translation and produces a ribozyme. In this embodiment, the selected polynucleotide is also positioned in a sense orientation with respect to the second promoter.

In still another alternative embodiment, the expression of the selected polynucleotide involves transcription but not translation and results in an RNA molecule—which serves as an antisense nucleic acid. In such an embodiment, the selected polynucleotide may be the target gene, or a fragment thereof, which is positioned in the expression construct in an antisense orientation with respect to said second promoter.

The expression construct may further comprise a gene encoding a selectable marker, such as hygromycin resistance, neomycin resistance, puromycin resistance, zeocin, gpt, DHFR, green fluorescent protein or histadinol.

Alternatively, the expression construct may further comprise (i) a second selected polynucleotide which is operably linked to said second promoter, and (ii) an internal ribosome entry site positioned between said first and second selected polynucleotides.

The cell may be a tumor cell, a cell located within a tumor, or a cell located within a mammal. The introduction of the expression construct into the cell may occur in vitro or in vivo. In an one embodiment, the introduction of the expression construct into the cell is mediated by a delivery vehicle selected from the group consisting of liposomes, retroviruses, adenoviruses, adeno-associated viruses, lentiviruses, herpes simplex viruses, and vaccinia viruses.

In another embodiment of the invention, a method of providing a subject with a therapeutically effective amount of a product of a selected gene is provided. This method involves providing a first expression construct which comprises an inducible promoter operably linked to a gene encoding a transactivating factor and providing a second expression construct which comprises a second promoter operably linked to a selected polynucleotide, where the second promoter is activated by the transactivating factor encoded by the first expression construct. The first and second expression construct are introduced into the desired cell of said subject and that cell is subjected to conditions which activate the inducible promoter, so that expression of the selected polynucleotide is induced. In a preferred embodiment, the first and second expression constructs are present on the same vector. Also, the inducible promoter is preferably a heat shock promoter, and the activating conditions comprise a temperature below 42° C. and above about basal temperature.

The introduction of one or both of the expression constructs may be performed either in vivo or ex vivo. The expression product of the selected polynucleotide may optionally be deleterious to a pathogen in the subject, such as a virus, bacterium, fungus, or parasite. Alternatively, the expression product of the selected polynucleotide may inhibit the growth of the cell of the subject. In still another alternative embodiment of the invention, the expression product of the selected polynucleotide replaces a deficient protein in the subject. Alternatively, the expression product of the selected polynucleotide may promote nerve regeneration.

In further embodiments, there is provided a method of treating cancer in a mammal, such as a human, comprising the steps of (a) providing one or more of the expression constructs described herein (b) introducing said expression construct into a tumor cell; and (c) subjecting the tumor cell to conditions which activate the inducible promoter, as described herein, so that the selected polynucleotide is expressed in high enough quantities to inhibit the growth of the tumor cell.

The cancer may optionally be selected from the group consisting of cancers of the brain, lung, liver, spleen, kidney, lymph node, small intestine, pancreas, blood cells; colon, stomach, breast, endometrium, prostate, testicle, ovary, vulva, cervix, skin, head and neck, esophagus, bone marrow and blood.

Methods for provoking an immune response in a mammal, such as a human, are also provided by the present invention. The provoked immune response may constitute either a humoral immune response or a cellular immune response. In one embodiment, the method comprises (a) providing one or more of the expression constructs described herein (b) introducing said expression construct into a cell in the mammal; and (c) subjecting the cell to conditions which activate the inducible promoter so that the selected polynucleotide is expressed highly enough to provoke an immune response in the mammal.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 9 shows amplifier constructs containing the therapeutic gene IL-2 driven by either the HIV-1 or the HIV 2 promoter. The amplifier part is controlled by either the CMV or the HSP 70 promoter driving TAT expression. The plasmids also contain the neomycin resistance gene and elements for growth in bacteria. These constructs were used in the amplifier studies of Examples 2 and 3.

FIG 10. shows the DNA sequence (SEQ ID NO:1) of the BamH 1-HindIII fragment of p1730R from StressGen Biotechnology Corp. This fragment contains the approximately 0.4 kb minimal HSP70B promoter fragment used in constructs of the specific examples, Example 1 and 3, below.

DESCRIPTION OF ILLUSTRATIVE EMBODIMENTS

1. The Present Invention

Figure 1:
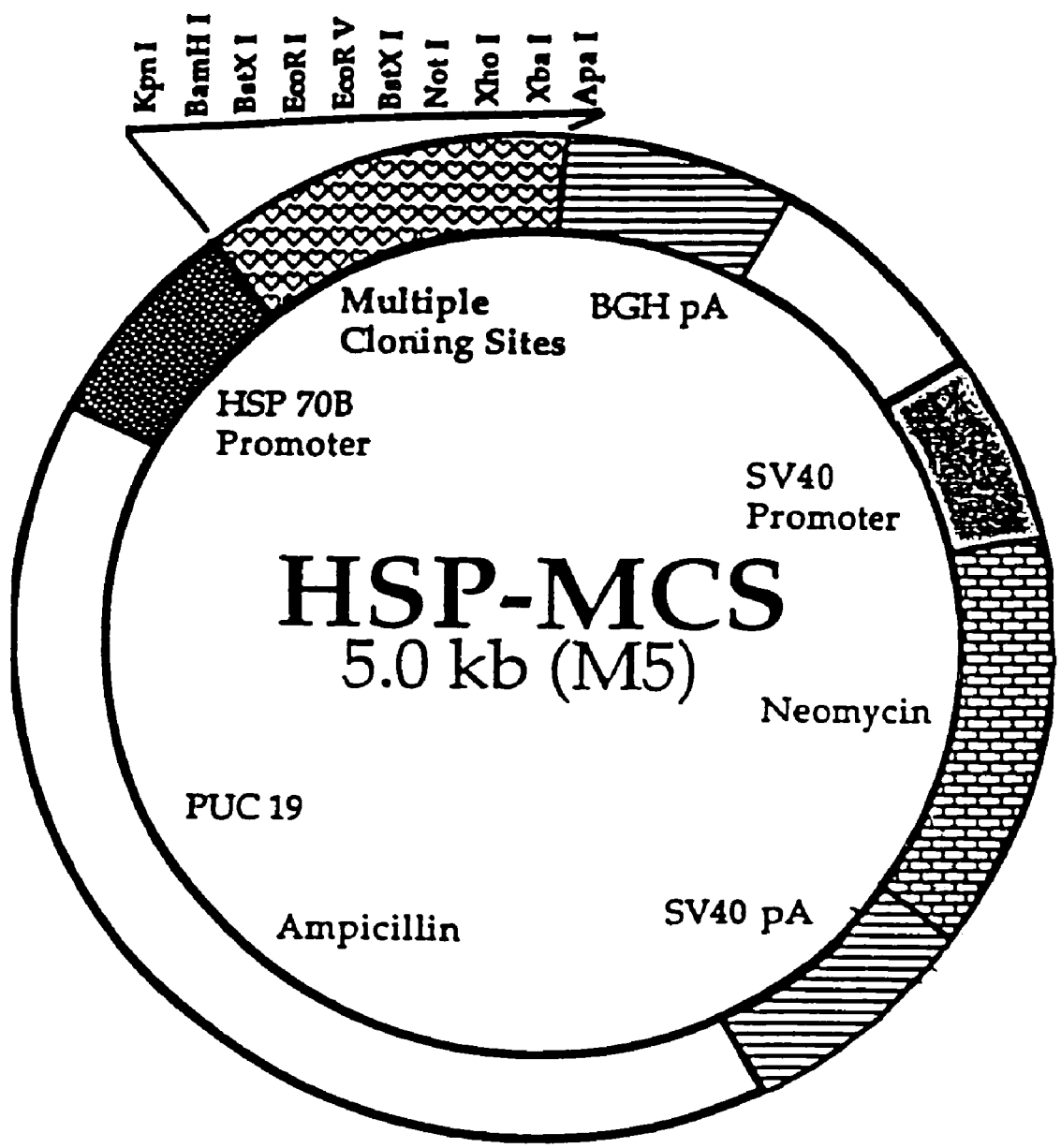
FIG. 1 depicts the basic vector used for quantitating heat shock promoter activity. The plasmid contains a minimal promoter derived from the HSP70B promoter (StressGen). A reporter gene, such as Enhanced Green Fluorescence Protein (EGFP), -gal, or IL-2 is easily inserted into the multiple cloning site (MCS) so that it is expressed under control of the minimal HSP70B promoter. The plasmid also contains the neomycin and ampicillin resistance genes for selectability in mammalian cells as well as the standard elements for growth in a bacterial system. The S8 plasmid comprises the plasmid shown with EGFP inserted in the multiple cloning site.

Gene therapy faces two major technical problems: how to both regulate and enhance the expression of therapeutic genes in vivo. The present invention addresses both of these questions by providing inducible expression constructs that can be induced by one or more of hyperthermia, chemotherapeutic agents, radiation, and immunotherapeutic agents. The inventors have demonstrated increases in the efficiency of specific, inducible gene expression using the combination of the expression constructs described herein with the inducing agents.

The ability to express therapeutic gene(s) at very high levels and the ability to control the levels of expression are important objectives in the development of gene therapy. The inventors have created new sets of expression vectors to address these objectives. In one embodiment, the inventors use an amplifier strategy to drive the expression of the gene(s) of interest. The amplifiers consist of, for example, the human HSP70B promoter driving expression of proteins that are transcriptional activators of other promoters, which, in turn, drive reporter genes. These additional promoters and their operably linked reporter genes are preferably included in the same vector with the HSP70B promoter element and the gene encoding the transactivating protein.

In another aspect of the invention, the expression constructs utilize the discovery that certain inducible promoters, e.g., heat shock promoters, can be induced to high levels when cells containing the expression constructs are treated with combinations of heat, radiation, and chemotherapeutic agents.

In transfection studies of mammalian cells using human IL-2 as the reporter gene, the inventors have shown that gene expression was dramatically increased using their amplifier constructs for all temperature conditions used, compared to reporter gene expression produced by the constitutive CMV promoter or by HSP70B alone (see example, Example 3, below). Constructs containing both the HSP70B promoter, upstream of the human immunodeficiency virus (HIV) tat gene, and the HIV1 or HIV2 long terminal repeats, upstream of the interleukin-2 (IL-2) gene, exhibited promoter activity at 37° C. which was further amplified by heat shock. Co-transfection experiments indicated that the activities of the HSP, HSP/HIV1 and HSP/HIV2 promoter expression constructs were 0.4, 6.9 and 83.3, respectively, times that of the CMV promoter expression construct in mammalian cells. These data indicate that, while less active than the CMV promoter by itself, this minimal heat shock promoter can be used in conjunction with a second promoter to markedly amplify gene expression while still maintaining some temperature dependence.

Earlier studies have examined the use of the heat shock promoter to drive the expression of transactivating proteins to conditionally express other promoters (Schweinfest et al., Gene, 71(1):207–210, 1988; EPO 01 18393; WO 89/00603, U.S. Pat. No. 5,614,381; U.S. Pat. No. 5,646,010; EP 0 299 127). The inventions described herein differ from these earlier approaches, for example, by use of 1) different heat shock promoters, (Schweinfest et al., use *Drosophila* promoters) 2) different modes of delivery (the present inventors have incorporated both promoters into a single construct— whereas others have used cotransfection) 3) different temperatures for induction (the earlier work used temperatures greater than 42° C., whereas the present invention advantageously operates at temperatures of 42° C. and lower); 4) use of radiation, chemotherapy, and/or immunotherapy combined with heat to provide high level inducible expression, and 5) use in gene therapy context rather industrial production. Furthermore, the present inventors are able to use either HIV-1 or HIV-2 promoters and the present invention shows a clear distinction in the expression levels resulting from these two promoters.

In a preferred aspect of the present invention, methods of effecting transgene expression in a mammalian cell by using a heat shock inducible element are provided. In one aspect of the invention, the heat shock sequence is used to drive the expression of a transactivating gene. Thus, when the expression construct is subjected to hyperthermia, the expression of the transactivating element is induced. The transactivating gene acts upon a second promoter which becomes activated to drive the expression of the therapeutic gene of interest. In a particular embodiment, a promoter derived from the HSP70 promoter is employed. A particularly useful aspect of this promoter is that it has a low basal level of expression at ambient temperatures and is inducible. The present invention further provides methods of providing a subject with a therapeutically effective amount of a gene product and for inhibiting the growth of a cell or provoking an immune response.

In a preferred embodiment of the present invention, the vector constructs described herein provide expression of the selected polynucleotides in an amounts of about at least 20-fold over that of the same selected polynucleotide expressed in a CMV promoter expression vector. In additional preferred embodiments, the level of expression is at least 30-fold, 35-fold, 40-fold, 45-fold, 50-fold, 55-fold, 60-fold, 65-fold and 70-fold over that of the same selected polynucleotide expressed in a CMV promoter expression vector.

Using the Enhanced Green Fluorescence Protein (EGFP) gene as a reporter gene, a human breast carcinoma cell line (MCF-7) was transfected with pHOT-EGFP and stably transfected cells selected with neomycin (See Example 8 below). The stable transfectants were subjected to three different experimental conditions; heat treatment at 42° C. for one hour, treatment with geldanamycin at 1 µg/ml (an anti-leukemic drug) or 3000 rads of gamma-radiation. EGFP expression was measured for up to 72 hours by flow cytometry. The inventors show that the non-treated cells expressed a basal level of EGFP that increased 387% above background at 24 hours after heat-shock. Cells treated with Geldanamycin had a 208% increase in EGFP intensity at 24 hours which was maintained up to 72 hours as compared to the non-treated cells. Exposure of cells to 3000 rads of gamma-radiation had a 150% increase in EGFP expression at 48 hours post-treatment as compared to the non-treated cells. Induction of heat shock proteins by heat, radiation and geldanamycin was confirmed by Western blot analysis. This inducible gene expression system may be applicable to clinical use in synergy with other types of standard therapy (e.g., hyperthermia, radiation and chemotherapy).

2. Heat Shock Response

The heat shock or stress response is a universal response occurring in organisms ranging from plants to primates. It is a response that can be elicited as a result of not only heat shock, but also as a result of a variety of other stresses including ischemia, anoxia, glucose deprivation, ionophores glucose and amino acid analogues, ethanol, transition series metals, drugs, hormones and bacterial and viral infections. Furthermore, there is evidence that overexpression of heat shock protein genes may be associated with enhanced proliferation and stress of tumor cells (Finch et al., *Cell Growth and Differentiation* 3(5):269–278, 1992). This response is characterized by the synthesis of a family of well conserved proteins of varying molecular sizes that are differently induced and localized. These proteins are among the most phylogenetically conserved and are characterized according to their weights.

The transcriptional activation of stress protein-encoding genes occurs within minutes in response to environmental and or physiological trauma. This speedy response has been attributed to the lack of introns in the vast majority of heat shock proteins. This absence of introns allows heat shock proteins to circumvent a block in intron processing that occurs at elevated temperature. Thus, the heat shock protein is translated with very high efficiency, often at the expense of other proteins.

The activation of the stress genes is mediated by the conversion of a pre-existing heat shock transcription factor (HSF) from an inactive to an active form. There is a large difference in the molecular weight of this DNA-binding protein (e.g., 83 kDa in humans and 150 kDa in yeast). The heat shock element is a conserved upstream regulatory sequence of HSP70 to which HSF binds. Although the main function of heat shock proteins is in facilitating protein folding and preventing aggregation, it is apparent that these proteins play some role in providing an organism with a protective mechanism against environmental insult and aid recovery subsequent to trauma.

Like most eukaryotic sequence-specific transcription factors, HSF acts through a highly conserved response element found in multiple copies upstream of the heat shock gene. The heat shock response element is composed of three contiguous inverted repeats of a 5-base pair sequence whose consensus was defined as nGAAn and more recently defined as AGAAn. The regulation of HSF primarily comprises a change in activity rather than an alteration in synthesis or stability.

3. Hyperthermia Therapy

Many clinical studies have shown the effectiveness of hyperthermia as an adjunctive treatment for malignancies, when used in combination with radiotherapy or chemotherapy (Hahn, G. M., Hyperthermia and Cancer, 2nd Ed., New York, Plenum, 1982; Scott, et al., Int. J. Rad. Oc. Biol. Phys. 10(11) 22192123, 1984; Lindholm, et al., Rec. Res. in Cancer Res. 107:152–156, 1988. The rationale for heat application, indication and contraindications, is developed on the basis of experimental evidence that desirable physiological responses can be produced by the use of heat and on the basis of controlled clinical studies. Lehman provides a comprehensive treatise for the therapeutic use of heat in other applications (Therapeutic Heat and Cold, Rehabilitation Medicine Library, published by Williams & Wilkins, 1990, incorporated by reference) the reader is referred in particular to Chapter 9, which discusses the use of heat in the context of therapeutic interventions, both medical and surgical.

"Hyperthermia" is intended to refer to a temperature condition that is greater than the ambient temperature of the subject to which the treatment is being administered. Hence, a hyperthermic temperature, as used herein, will typically range from between about 37° C. to about 42° C. In preferred embodiments, the temperature will range from about 38° C. to about 42° C., in other embodiments, the temperature range will be from about 39° C. to about 41° C., in other embodiments, the temperature will be about 40° C. With the devices currently available for the application of hyperthermia in adjuvant therapies it is possible to maintain the temperature of hyperthermia treatment to within about 0.5° C. for temperatures up to 42° C. Hence, the therapeutic treatments of the present invention may be carried out at 37.0° C., 37.2° C., 37.4° C., 37.6° C., 37.8° C., 38.2° C., 38.4° C., 38.6° C., 38.8° C., 39.2° C., 39.4° C., 39.6° C., 39.8° C., 40.2° C., 40.4° C., 40.6° C., 40.8° C., 41.2° C., 41.4° C., 41.6° C., 41.8° C., or 42.0° C. Prior to the present invention, efficacy of hyperthermia required that temperatures within a tumor(s) remain above about 43° C. for 30 to 60 min, while safety considerations limit temperatures in normal tissues to below 42° C. Achieving uniform temperatures above 42° C. in tumors is very difficult and often not possible.

Tissues in mammals can be heated using a number of technologies including ultrasound, electromagnetic techniques, including either propagated wave (e.g., microwaves), resistive (e.g., radiofrequency) or inductive (radiofrequency or magnetic) procedures (Hahn, G. M., Hyperthermia and Cancer, 2nd Ed., New York, Plenum, 1982; Lehman, L. B., Postgard Med., 88(3):240–243, 1990; both herein incorporated by reference). In some simple applications, tissue temperatures can be elevated using circulated hot air or water.

U.S. Pat. No. 4,230,129 to Le Veen, herein incorporated by reference, refers to a method of heating body tissue and monitoring temperature changes in the tumor in real time with the aid of a scintillation detector. The method provides for the coupling of radiofrequency (RF) energy to the patient's body to avoid any significant heat absorption in the fatty tissues. This is obtained by focusing the RF energy on the tumor with an orbital movement of the applicator so that energy is not constantly being applied to the same confined area within the patient's body. U.S. Pat. No. 3,991,770 to Le Veen, also herein incorporated by reference, teaches a method of treating a tumor in a human by placing the part of the human body containing the tumor in a radiofrequency electromagnetic field to heat the tumor tissue and cause necrosis of the tumor without damaging the adjacent normal tissue.

In preferred embodiments, of the present invention, hyperthermia is applied in combination with the gene therapy vectors disclosed herein to achieve inducible gene expression at a particular tumor site. Furthermore, the hyperthermia/gene therapy treatment regimens may be used in combination with other conventional therapies, such as the chemotherapies and radiotherapies discussed below, to effectively treat cancer. Other methods for inducing hyperthermia also are known in the art. Methods and devices for the regional and/or systemic application of hyperthermia are well know to those of skill in the art and are disclosed in for example, U.S. Pat. Nos. 5,284,144; 4,230,129; 4,186,729; 4,346,716; 4,848,362; 4,815,479; 4,632,128, all incorporated herein by reference.

4. Promoter Induction and Combination Therapy

The expression constructs of the present invention may advantageously be induced by combining the hyperthermia treatments described above with one or more of chemo-, radio-, and/or immunotherapies. This provides the advantage of combining therapies such as chemo- and radiotherapy with gene therapy. For example, the herpes simplex-thymidine kinase (HS-tk) gene, when delivered to brain tumors by a retroviral vector system, successfully induces susceptibility to the antiviral agent ganciclovir. However, the effective use of gene therapy in combination with traditional cancer therapies has been hindered by the need for clinically significant expression of the genes once they have been transferred to the target cell.

Thus, to kill cells, inhibit cell growth, inhibit metastasis, decrease tumor size and otherwise reverse or reduce the malignant phenotype of tumor cells, using the methods and compositions described herein, the expression construct can be introduced into the cell, and induce expression by hyperthermia and/or combined with one or more of the chemo-, radio-, and/or immunotherapies described herein. This has the advantage of both providing the conventional chemo-, radio-, and/or immunotherapies used in cancer treatments with the discovery that therapeutic amounts of a gene can be significantly induced by these chemo-, radio-, and/or immunotherapies when combined with hyperthermia. Thus, the combination of therapies would be provided in an amount sufficient to to kill cells, inhibit cell growth, inhibit metastasis, decrease tumor size and otherwise reverse or reduce the malignant phenotype of tumor cells.

In preferred embodiments, the combined therapy would be conducted for as long as required to achieve the desired effect. For example, after the expression constructs have been introduced into cells, it is contemplated that the cells containing the expression construct will induced within about 12–24 hours of each other and, more preferably, within about 6–12 hours of each other, however, it may be desirable to extend this time to several days (2, 3, 4, 5, 6 or 7) to several weeks (1, 2, 3, 4, 5, 6, 7 or 8).

Agents or factors suitable for use in the present invention are any chemical compound or treatment method that induces DNA damage when applied to a cell. Such agents and factors include radiation and waves that induce DNA damage such as, γ-irradiation, X-rays; UV-irradiation, microwaves, electronic emissions, and the like.

In one embodiment of the invention, the radiation therapy constitutes external beam radiation. The external beam radiation treatment typically delivers high-energy radiation, such as high-energy x-ray beams.

Alternatively, internal radiation, or brachytherapy, may be used. Methods of delivering brachytherapy include intracavitary or interstitial placement of radiation sources, instillation of colloidal solutions, and parenteral or oral administration. Sealed sources are encapsulated in a metal, wire, tube, needle, or the like. Unsealed radioactive sources are prepared in a suspension or solution.

Encapsulated radioactive elements are placed in body cavities or inserted directly into tissues with suitable applicators. The applicator is usually placed into the body cavity or tissue surgically or using fluoroscopy. The applicators; usually plastic or metal tubes, may be sutured into or near the tumor to hold them in place. The radioactive isotope is later placed into the applicator ("afterloading"). Radiative implants are used in the treatment of cancers of the tongue, lip, breast, vagina, cervix, endometrium, rectum, bladder, and brain. Encapsulated sources may also be left within a patient as permanent implants. "Seeding" with small beads of radioactive material is an approach used for the treatment of localized prostate cancers, and localized, but inoperable, lung cancers.

A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP), geldanamycin, and even hydrogen peroxide. The invention also encompasses, the use of a combination of one or more DNA damaging agents, whether radiation-based or actual compounds, such as the use of X-rays with cisplatin or the use of cisplatin with etoposide. These and other agents are described in These and other agents are described in Handbook of Medical Oncology, Bonadonna and Robustelli della Cuna, Year Book Medical Publishers, Inc. Chicago, Ill. (1988), which is incorporated herein by reference; and also adriamycin: Jones et al., Cancer 36:90–97, 1975; Gutterman et al., Brit. Med. J. 2:1222–4, 1976; 5-fluorouracil (5FU): Canellos et al., Cancer 38:1882–6, 1976 and Bull et al., Cancer 41:1649–57, 1978; etoposide (VP-16): Evens et al., J. Clin. Oncol.3:1471–77, 1985 and Newlands et al., Br. J. Obst.Gynaecol. 93:63–69, 1986; actinomycin-D: Vugrin et al., Ann. Intern. Med.95:59–61, 1981 and Goldstein et al., Sem. Oncol. 9:191–7,1982; mitomycin C: Alberts et al., Cancer Clin. Trials 4:313–16, 1981 and Bukowsky et al., Cancer Clin. Trials 3:321–4, 1980; cisplatin (CDDP): Rooney et al., Cancer 55:1123–28,1985 and Gralla et al., Ann. Intern. Med. 95:414–20,1981; geldanamycin: Schnur et al., J Med Chem 38:3806–12, 1995, and Egorin et al. Cancer Res, 58:2385–96, 1998 and Kelland et al., J Natl Cancer Inst 91:1940–49, 1999.

Agents that directly cross-link nucleic acids, specifically DNA, are envisaged to facilitate DNA damage leading to a synergistic, antineoplastic combination with the expression constructs of the present invention. Agents such as cisplatin, and other DNA alkylating agents may be used. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, veraparnil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 100 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as-5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 450–1000 mg/m2/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The regional delivery of the therapeutic expression constructs of the present invention to patients with cancers is a preferred method for delivering a therapeutically effective gene to counteract the clinical disease being treated. Similarly, the chemo- or radiotherapy may be directed to a particular, affected region of the subject's body. Alternatively, systemic delivery of expression construct and/or the agent may be appropriate in certain circumstances, for example, where extensive metastasis has occurred.

In addition to combinations of gene therapies with chemo- and radiotherapies, it also is contemplated that combination of multiple gene therapies will be advantageous. For example, targeting of p53 and p16 mutations at the same time may produce an improved anti-cancer treatment. Any other tumor-related gene conceivably can be targeted in this manner, for example, p21, Rb, APC, DCC, NF-1, NF-2, BRCA2, p16, FIRT, WT-1, MEN-I, MEN-II, BRCA1, VHL, FCC, MCC, ras, myc, neu, raf, erb, src, fms, jun, trl, ret, gsp, hst, bcl and abl.

5. Engineering Expression Constructs

In certain embodiments, the present invention involves the manipulation of genetic material to produce expression constructs that encode therapeutic genes. Such methods involve the use of an expression construct containing, for example, a heterologous DNA encoding a gene of interest and a means for its expression, replicating the vector in an appropriate helper cell, obtaining viral particles produced therefrom, and infecting cells with the recombinant virus particles. The gene will be a therapeutic gene, for example to treat cancer cells, to express immunomodulatory genes to fight viral infections, or to replace a gene's function as a result of a genetic defect. In the context of the gene therapy vector, the gene will be a heterologous DNA, meant to include DNA derived from a source other than the viral genome which provides the backbone of the vector. Finally, the virus may act as a live viral vaccine and express an antigen of interest for the production of antibodies there against. The gene may be derived from a prokaryotic or eukaryotic source such as a bacterium, a virus, a yeast, a parasite, a plant, or an animal. The heterologous DNA also may be derived from more than one source, i.e., a multigene construct or a fusion protein. The heterologous DNA also may include a regulatory sequence which may be derived from one source and the gene from a different source.

a) Therapeutic Genes

The selected polynucleotide of the present invention may optionally be a therapeutic gene. Any of a wide variety of therapeutic genes are suitable for use in the vectors and methods described herein. Therapeutic genes which are suitable for application of the present invention to a particular disorder, medical condition, or disease will be discernible to one skilled in the art.

In one embodiment of the invention, the selected polynucleotide is the gene encoding for ornithine decarboxylase antizyme protein. The ornithine decarboxylase (ODC) antizyme protein is an important component of feedback regulation of intracellular polyamine pool sizes (Hayashi et al., Trends in Biochemical Sciences 21(1):27–30, 1996, herein incorporated by reference). The levels of this protein are directly related to levels of intracellular polyamines, which stimulate translation of antizyme message. Antizyme protein targets ornithine decarboxylase, the first and often rate-limiting enzyme in polyamine synthesis, for degradation. This protein also suppresses polyamine uptake. Thus, low levels of endogenous polyamines lead to low levels of antizyme which in turn maximizes polyamine synthesis via ODC and polyamine uptake. Conversely, high levels of endogenous polyamines cause high levels of antizyme protein, which in turn minimize polyamine synthesis via ODC and suppress polyamine uptake.

The radioprotector WR-33278 (N,N"-(dithiodi-2,1-ethanediyl)bis-1,3-propanediamine) is a disulfide-containing polyamine analog, which is taken up by cells using the polyamine transporter (Mitchell et al., Carcinogenesis, 16:30633068, 1995, herein incorporated by reference). This transporter is inhibited by antizyme. Evidence from animal models indicates that this radioprotector is taken up by at least some normal tissues to a greater extent than some tumors (Ito et al., International Journal of Radiation Oncology, Biology, Physics 28:899–903, 1994). Agents like WR-33278 have been used in clinical radiotherapy in attempts to protect dose-limiting normal tissues from toxicity, without reducing the tumor control effectiveness of radiotherapy (Spencer and Goa, Drugs, 50(6):1001–31, 1995, herein incorporated by reference). Rationale for the difference in uptake of VWR-33278 may be that proliferating tumor cells often contain higher levels of polyamines than do non-proliferating cells in normal tissues. Thus, tumors would express higher levels of antizyme than would normal tissues.

The inventors have placed an antizyme cDNA lacking the sequences necessary for polyamine-dependent regulation under the control of the human heat shock 70B promoter. The inventors have stably transfected human prostate cancer derived DU-145 cells with this construct and have selected clones which display heat-inducible suppression of polyamine uptake (indicating heat-inducible antizyme activity). The therapeutic application of this gene therapy (HSP70B promoter regulation of antizyme expression) will be put to use in future clinical trials in men with localized prostate cancer. Patients are treated with this gene therapy, administered intratumorally, combined with systemic WR-33278 and localized radiotherapy. Expression of antizyme intratumorally is then activated by localized hyperthermia. Dose-limiting normal tissues adjacent to these prostate tumors will not express antizyme in response to hyperthermia and will take up the radioprotector VWR-33278, while the tumor tissue will not take up the radioprotector because they will express antizyme in response to hyperthermia. This strategy will allow higher doses of radiotherapy to be given to the prostate, with the intent to improve local control of prostate cancers.

In an alternative embodiment, other metabolic products of the cytoprotective drug ethyol (also known as amifostine, VVR-2721, or S-2-(3-aminopropylamino)ethylphosphororthioic acid) other than WR33278 may be used in conjunction with the expression constructs described herein. For instance, WR-1065 (2-(3-aminopropylamino)ethanethiol) may be instead used as the radioprotector.

There are many other genes that may be delivered using the vectors of the present invention. For instance, it is contemplated that the vectors of the present invention may be used to transfer tumor suppressors, antisense oncogenes and prodrug activators, such as the HSV-TK gene (Rosenfeld et al., Annals of Surgery, 225:609–618, 1997; Esandi et al., Gene Therapy, 4:280–287, 1997), for the treatment of cancer. Other genes which could optionally be used in the expression constructs of the present invention include p53, p16, p21, p27, C-CAM, HLA-B7 (Gleich, et al., Arch Otolaryngol Head Neck Surg, 124:1097–104, 1998; Heo et al., Hum. Gene Ther. 9:2031–8, 1998; Nabel et al., Proc. Nat. Acad. Sciences USA, 90:15388–15393, 1996; Stopeck et al., Journal of Clinical Oncology, 15:341–349, 1997), IL2 (O'Malley et al., Molecular Endocrinology, 11:667–673, 1997; Otova et al., Folia Biologica, 43:25–32, 1997), IL4 (Klieg, Nature Biotechnology, 15:316–317, 1997), IL7 (Toloza et al., Annals of Surgical Oncology, 4:70–79, 1997; Sharma et al., Cancer Gene Therapy, 3:303–313, 1996), IL12 (Hiscox and Jiang, In Vivo, 11:125–137, 1997; Chen-etal., Journal of Immunology, 159:351–359, 1997), GM-CSF (Kreitman and Pastas, Blood, 90:252259, 1997; Homick et al., Blood, 89:4437–4.447, 1997; Lama. et al., Haematologica, 82:239–245, 1997), IFN (Noguchi et al., Clinical Infectious Diseases, 24:992–994, 1997; Kanemaru et al., European Archives of Oto-Rhino-Laryngology, 254:158–162, 1997; Tanaka et al., Journal of Gastroenterology and Hepatology, 11:1155–1160, 1996; Imai et al., Liver, 17:88–92, 1997), I-CAM1, and TNF (Corcione et al., Annals of the New York Academy of Sciences, 815:364366, 1997). (All articles cited in this paragraph are herein incorporated by reference.)

p53 currently is recognized as a tumor suppressor gene (Montenarh, Crit.Rev. Oncogen, 3:233–256, 1992). High levels of mutant p53 have been found in many cells transformed by chemical carcinogenesis, ultraviolet radiation, and several viruses, including SV40. The p53 gene is a frequent target of mutational inactivation in a wide variety of human tumors and already is documented to be the most frequently-mutated gene in common human cancers. It is mutated in over 50% of human NSCLC and in a wide spectrum of other tumors.

$P16^{ink4}$ belongs to a newly described class of CDK-inhibitory proteins that also includes $p16^B$, $p221^{WAF1, CIP1, sDn}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines. Restoration of wild-type $p16^{INK4}$ function by transfection with a plasmid expression vector reduced colony formation by some human cancer cell lines (Okamoto, et al., Proc. Nati. Acad. Sci. USA, 91:11045–11049, 1994; Arap, et al., Cancer Res., 55:1351–1354, 1995, both herein incorporated by reference).

C-CAM is expressed in virtually all epithelial cells. C-CAM, with an apparent molecular weight of 105 kD, originally was isolated from the plasma membrane of the rat hepatocyte by its reaction with specific antibodies that neutralize cell aggregation. Recent studies indicate that, structurally, C-CAM belongs to the immunoglobulin (Ig) superfamily and its sequence is highly homologous to carcinoembryonic antigen (CEA). The first Ig domain of C-CAM has been shown to be critical for cell adhesion activity.

Cell adhesion molecules, or CAMs are known to be involved in a complex network of molecular interactions that regulate organ development and cell differentiation (Edelman, Annu. Rev. Biochem., 54:135–169, 1985). Recent data indicate that aberrant expression of CAMs may be involved in the tumorigenesis of several neoplasms; for example, decreased expression of E-cadherin, which predominantly is expressed in epithelial cells, is associated with the progression of several kinds of neoplasms. Also, Giancotti and Ruoslahti, Cell, 60:849–859, 1990, incorporated herein by reference, demonstrated that increasing expression of $_{5\ 1}$ integrin by gene transfer can reduce tumorigenicity of Chinese hamster ovary cells in vivo. C-CAM now has been shown to suppress tumor growth in vitro and in vivo.

Other tumor suppressors that may be employed according to the present invention. For example, the selected polynucleotide may be any one of the following genes: retinoblastoma (Rb); adenomatous polyposis coli gene (APC); deleted in colorectal carcinomas (DCC); neurofibromatosis 1 (NF-1); neurofibromatosis 2 (NF-2); Wilm's tumor suppressor gene (WT-1); multiple endocrine neoplasia type 1 (MEN-1); multiple endocrine neoplasia type 2 (MEN2); BRCA1; von Hippel-Lindau syndrome (VHL); mutated in colorectal cancer (MCC); p 16; p21; p57; p27; and BRCA2.

In an alternative embodiment of the invention, the methods and vectors of the present invention may be used to promote regeneration processes, such as nerve regeneration, by stimulating the production of growth factors or cytokines. In such an embodiment the selected polynucleotide may be a neurotrophic factor. For instance, the selected polynucleotide may encode ciliary neurotrophic factor (CNTF), brain-derived neurotrophic factor (BDNF), or glial cell line-derived neurotrophic factor (GDNF) (Mitsumoto et al., Science, 265:1107–1110, 1994 and Gash et al., Ann. Neurol., 44(3 Suppl 1):S 121–125, 1998, both herein incorporated by reference). Alternatively, the selected polynucleotide of the expression construct may optionally encode tyrosine hydroxylase, GTP cyclohydrolase 1, or aromatic L-amino acid decarboxylase (Kung, Mov. Disord., 13 Suppl 1:59–72, 1998, herein incorporated by reference). In still another embodiment, the therapeutic expression construct may express; a growth factor such as insulin-like growth factor-I (IGF-I) (Webster, Mult. Scler., 3:113–120, 1997, incorporated herein by reference).

Examples of other diseases for which the present vectors are useful include but are not limited to hyperproliferative diseases and disorders, such as rheumatoid arthritis or restenosis by transfer of therapeutic genes, e.g., gene encoding angiogenesis inhibitors or cell cycle inhibitors.

b) Antisense Constructs

Oncogenes such as ras, myc, neu, raf, erb, src, fms, jun, trk, ret, gsp, hst, bcl and abl also are suitable targets. However, for therapeutic benefit, these oncogenes would be expressed as an antisense nucleic acid, so as to inhibit the expression of the oncogene. The term "antisense nucleic acid" is intended to refer to the oligonucleotides complementary to the base sequences of oncogene-encoding DNA and RNA. Antisense nucleic acid, when expressed in a target cell, specifically bind to their target nucleic acid and interfere with transcription, RNA processing, transport and/or translation. Targeting double-stranded (ds) DNA with polynucleotides leads to triple-helix formation; targeting RNA will lead to double) helix formation.

Antisense constructs may be designed to bind to the promoter and other control regions, exons, introns or even exon-intron boundaries of a gene. Antisense RNA constructs, or DNA encoding such antisense RNAS, may be employed to inhibit gene transcription or translation or both within a host cell, either in vitro or in vivo, such as within a host animal, including a human subject. Nucleic acid sequences comprising "complementary nucleotides" are those which are capable of base-pairing according to the standard Watson-Crick complementary rules. That is, that the larger purines will base pair with the smaller pyrimidines to form only combinations of guanine paired with cytosine (G:C) and adenine paired with either thymine (A:T), in the case of DNA, or adenine paired with uracil (A:U) in the case of RNA.

As used herein, the terms "complementary" or "antisense sequences" mean nucleic acid sequences that are substantially complementary over their entire length and have very few base mismatches. For example, nucleic acid sequences of fifteen bases in length may be termed complementary when they have a complementary nucleotide at thirteen or fourteen positions with only single or double mismatches. Naturally, nucleic acid sequences which are "completely complementary" will be nucleic acid sequences which are entirely complementary throughout their entire length and have no base mismatches.

While all or part of the gene sequence may be employed in the context of antisense construction, statistically, any sequence 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent 5 antisense inhibitors of gene expression (Wagner et al., Science, 260:1510–1513, 1993, herein incorporated by reference).

c) Ribozyme Constructs

As an alternative to targeted antisense delivery, targeted ribozymes may be used. The term "ribozyme" refers to an RNA-based enzyme capable of targeting and cleaving particular base sequences in DNA or, more typically, RNA. In the present invention, ribozymes are introduced into the cell as an expression construct encoding the desired ribozymal RNA. The targets of the ribozymes are much the same as described for antisense nucleic acids.

Many ribozymes are known to catalyze the hydrolysis of phosphodiester bonds under physiological conditions. The ribozymes of the present invention catalyze the sequence specific cleavage of a second nucleic acid molecule, preferably an mRNA transcript, and optionally an mRNA transcript of an oncogene. In general, ribozymes bind to a target RNA through the target binding portion of the ribozyme which flanks the enzymatic portion of the ribozyme. The enzymatic portion of the ribozyme cleaves the target RNA. Strategic cleavage of a target RNA destroys its ability to directly or indirectly encode protein. After enzymatic cleavage of the target has occurred, the ribozyme is released from the target and searches for another target where the process is repeated.

In a preferred embodiment of the invention, the ribozyme is a hammerhead ribozyme, a small RNA molecule derived from plant viroids (Symons, Ann. Rev. Biochem. 61: 641–671, 1992; Clouet-D'Orval and Uhlenbeck, RNA, 2:483–491, 1996; Haseloff and Gerlach, Nature 334:585–591, 1988; Jeffries and Symons, Nucleic Acids Res. 17: 1371–1377, 1989; Uhlenbeck, Nature 328:596–600, 1987; all herein incorporated by reference).

In other embodiments, the ribozyme may be a group I intron, a hairpin ribozyme, VS RNA, a hepatitis Delta virus ribozyme or an Rnase P-RNA ribozyme (in association with an RNA guide sequence). Examples of hairpin motifs are described by Hampel et al., Nucleic Acids Res. 18:299, 1990 and Hampel and Tritz, Biochemistry 28:4929, 1989; an example of the hepatitis delta virus motif is described by Perrotta and Been, Biochemistry 31:16, 1992; an example of the RNAseP motif (associated with an external guide sequence) is described by Yuan et al., U.S. Pat. No. 5,624,824; a Neurospora VS RNA ribozyme motif is described in Saville and Collies, Cell 61: 685–696, 1990, Saville and Collies, Proc. Natl. Acad. Sci. USA 88: 8826–8830, 1991, Collies and Olive, Biochemistry 32: 2795–2799, 1993; the group I intron is described in Cech et al., U.S. Pat. No. 5,354,855. The above-mentioned motifs should not be considered limiting with respect to the present invention and those skilled in the art will recognize that ribozymes that may be utilized herein comprise a specific substrate binding site which is complementary to a target mRNA. Such ribozymes also comprise an enzymatic portion which imparts RNA cleaving activity to the molecule. The enzymatic portion resides within or surrounds the substrate binding site.

d) Selectable Markers

In certain embodiments of the invention, the therapeutic vectors of the present invention contain nucleic acid constructs whose expression may be identified in vitro or in vivo by including a marker in the expression construct. Such markers would confer an identifiable change to the cell permitting easy identification of cells containing the expression construct. Usually the inclusion of a drug selection marker aids in cloning and in the selection of transfortnants. For example, genes that confer resistance to neomycin, puromycin, hygromycin, DHFR, GPT, zeocin, kanamycin, and histidinol are useful selectable markers.

Alternatively, enzymes such as herpes simplex virus thymidine kinase (tk) may be employed.

Immunologic markers also can be employed. The selectable marker employed is not believed to be important, so long as it is capable of being expressed simultaneously with the nucleic acid encoding a gene product. Further examples of selectable markers are well known to one of skill in the art and include reporters such as EGFP, β-gal and chloramphenicol acetyltransferase (CAT).

In one embodiment of the present invention, the selectable markers as two or more markers are provided in a single encoding DNA molecule, which allows the constructs to be reduced in size relative to those vectors containing two selectable markers in two separately controlled transcriptional units. For example, kanamycin and neomycin can be provided in a single transcript controlled by a single promoter.

e) Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites. IRES elements from two members of the picarnovirus family (polio and encephalomyocarditis) have been described (Pelletier and Sonenberg, Nature, 334:320–325, 1988), as well as an IRES from a mammalian message (Macejak and Sarnow, Nature, 353:90–94, 1991). IRES elements can be linked to heterologous open reading frames. Multiple open reading frames can be transcribed together, each separated by an IRES, creating polycistronic messages. By virtue of the IRES element, each open reading frame is accessible to, ribosomes for efficient translation. Multiple genes can thus be efficiently expressed using a single promoter/enhancer to transcribe a single message.

Any heterologous open reading frame can be linked to IRES elements. This includes genes for secreted proteins, multi-subunit proteins encoded by independent genes, intracellular or membrane-bound proteins and selectable markers.

f) Control Regions

In order for the expression construct to affect expression of a transcript encoding a therapeutic gene, the polynucleotide encoding the therapeutic gene will be under the transcriptional control of a promoter and a polyadenylation signal. A "promoter" refers to a DNA sequence recognized by the synthetic machinery of the host cell, or introduced synthetic machinery, that is required to initiate the specific transcription of a gene. A polyadenylation signal refers to a DNA sequence recognized by the synthetic machinery of the host cell, or introduced synthetic machinery, that is required to direct the addition of a series of nucleotides on the end of the mRNA transcript for proper processing and trafficking of the transcript out of the nucleus into the cytoplasm for translation. The phrase "under transcriptional control" means that the promoter is in the correct location in relation to the polynucleotide to control RNA polymerase initiation and expression of the polynucleotide.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and, SV40 early transcription units. These studies, augmented by more recent work; have shown that promoters are composed of discrete functional modules, each consisting of approximately 7–20 by of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 by apart before activity begins to decline. Depending on the promoter, it appears that individual elements can function either cooperatively or independently to activate transcription.

Where a human cell is targeted, it is preferable to position the polynucleotide coding region adjacent to and under the control of a promoter that is capable of being expressed in a human cell. Generally speaking, such a promoter might include either a human or viral promoter. A list of promoters is provided in Table 1.

TABLE 1

| PROMOTER |
| --- |
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class 115 |
| MHC Class II HLA-DR |
| β-Actin |
| Muscle Creatine Kinase |
| Prealbumin (Transthyretin) |
| Elastase I |
| Metallothionein |
| Collagenase |
| Albumin Gene |
| α-Fetaprotein |
| τ-Globin |
| β-Globin |
| c-fos |
| c-HA-ras |
| Insulin |
| Neural Cell Adhesion Molecule (NCAM) |
| $_1$Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

The particular promoter that is employed to control the expression of the therapeutic gene in the amplifier construct is not believed to be critical, so long as it is capable of being activated by the gene product linked to the inducible promoter. In a preferred embodiment of the invention, the transactivating protein is tat, and the promoter which is operably linked to the therapeutic gene is the HIV-1 or HIV-2 LTRs. For example, a promoter element containing an AP-1 site would respond to the inducible expression of the c-jun or c-fos proteins. Other suitable transactivating factor/promoter combination would be known by one skilled in the art.

The promoter which controls expression of the gene encoding the transactivating factor must be an inducible promoter. Likewise, in other embodied expression constructs, the therapeutic gene is controlled directly by the inducible promoter.

An inducible promoter is a promoter which is inactive or exhibits relatively low activity except in the presence of an inducer substance. Some examples of promoters that may be included as a part of the present invention include, but are not limited to; MT II, MMTV, collagenase, stromelysin, SV40, murine MX gene, α-2-macroglobulin, MHC class I gene h-2 kb, proliferin, tumor necrosis factor, or thyroid stimulating hormone gene. The associated inducers of these promoter elements are shown in Table 2. The Egr-1 promoter and the multidrug resistance gene (MDR1) promoter are also options for inducible promoters. In preferred embodiments the inducible promoter is heat shock inducible and is derived from one of the following promoters: HSP70, HSP70B, HSP90, HSP60, HSP27, HSP72, HSP73, HSP25, ubiquitin, and HSP28. In another preferred embodiment, the inducible promoter comprises a hypoxia-responsive element, such as those responsive to HIF-1. It is understood that any inducible promoter may be used in the practice of the present invention and that all such promoters would fall within the spirit and scope of the claimed invention.

In one embodiment of the invention a non-coding or non-transcriptionally active DNA sequence is provide between the inducible promoter and the transactivating factor encoding DNA sequence. Such a non-coding or non-transcriptionally active DNA sequence can be from about 100 base pairs to about 1.0 kilobases in length. "non-coding DNA sequence" as used herein means a DNA sequence that does not encode a given polypeptide or ribozyme, for example. A "non-transcriptional active DNA sequence" as used herein means a DNA sequence which does not direct the binding of one or more transcriptional proteins, which modulate, either up or down, the activity of an RNA polymerase as it synthesizes an RNA transcript from a DNA molecule.

TABLE 2

| Element | Inducer |
| --- | --- |
| MT II | Phorbol Ester (TPA) |
|  | Heavy metals |
| MMTV (mouse mammary tumor virus) | Glucocorticoids |
| β-Interferon | poly(rI)X poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2 Macroglobulin | IL-6 |
| Vimentin | Serum |
| MHC Class I Gene H-2kB | Interferon |
| HSP70 | Ela, SV40 Large T Antigen |
| Proliferin | Phobol Ester-TPa |
| Tumor Necrosis Factor | FMA |
| Thyroid Stimulating Hormone Gene | Thyroid Hormone |

In particularly preferred embodiments, the tat protein is used as the transactivating factor. The genome of HIV-1 and HIV-2 share a great deal of similarities with the Simian immunodeficiency viruses (SIVS) and they have been extensively studied. It was discovered that in addition to the gag, env, pol genes that are common to all retroviruses, there are a number of regulatory genes that are important in HIV transcription. The viral tat protein is one such regulatory factor and it is characterized by its ability to greatly increase the activity of the HIV-1 and HIV-2 promoter (Sodroski et al., J. Tirol, 55(3):831–835, 1985a; Sodroski, et al., Science, 229(4708):74–77, 1985b; Sodroski, et al., Science, 228 (4706):1430–1434, Sodroski, et al., Science, 228(4706): 1430–1434, 1985c; Sodroski et al., Science, 227(4683): 171–173, 1985d; which are all incorporated by reference herein). Tat is thought to bind with the transactivation response element (TAR) in the HIV LTR and increase the steady state levels of the HIV specific RNA. There is also evidence suggesting that tat can act more like a traditional transcription factor in that it can interact with several transactivator proteins. Tat and adenovirus transactivator EIA can act synergistically in increasing the levels of steady state RNA (Laspia et al., Genes Dev, 4(12B):2397–2408, 1990, herein incorporated by reference). Thus, a way to increase further the activity of the HIV-LTR/TAT constructs is to incorporate EIA into the same construct.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed. Such polyadenylation signals as that from SV40, bovine growth hormone, and the herpes simplex virus thymidine kinase gene have been found to function well in a number of target cells.

The vector can also contain appropriate polyadenylation sequences at the 3' end of each of the DNA sequences that encode a protein, e.g., transactivating factor, therapeutic protein and selectable marker. Such polyadenylation sequences are those that are composed primarily of Adenine and Thymine (DNA) or Uracil (RNA) nucleotides, examples of which are the SV40 polyadenylation sequence and the BGH polyadenylation sequence.

6. Methods of Gene Transfer

In order to effect transgene expression in a cell, it is necessary to first introduce or transfer the therapeutic expression constructs of the present invention into a cell. Such transfer may employ viral or non-viral methods of gene transfer. This section provides a discussion of methods and compositions of gene transfer.

A. Non-Viral Transfer

In a preferred embodiment, the therapeutic constructs of the present invention e.g., various genetic (i.e., DNA) constructs must be delivered into a cell. In certain preferred situations, the introduction of the expression construct into a cell is mediated by non-viral means.

Several non-viral methods for the transfer of expression constructs into cultured mammalian cells are contemplated by the present invention. These include calcium phosphate precipitation (Graham and Van Der Eb, Virology, 52:456–4.67, 1973; Chen and Okayama, Mol. Cell. Biol., 7:2745–2752, 1987; Rippe et al., Mol. Cell Biol., 10:689–695, 1990) DEAF-dextran (Gopal, Mol. Cell Biol, 5:1188–1190, 1985), electroporation (Tur-Kaspa et al., Mol. Cell Biol., 6:716–718, 1986; Potter eral., Proc. Nat. Acad. Sci. USA, 81:7161:7165, 1984), direct microinjection (Harland and Weintraub, J. Cell Biol, 10 1: 1094–1099, 1985), DNA-loaded liposomes (Nicolau and Sene, Biochim. Biophys. Acta, 721:185–190, 1982; Fraley et al., Proc. Natl. Acad. Sci. USA, 76:3348–3352, 1979), cell sonication (Fechheimer et al., Proc. Nad. Acad. Sci. USA, 84:84638467, 1987), gene bombardment using high velocity microprojectiles (Yang et al., Proc. Natl. Acad. Sci. USA, 87:9568–9572, 1990), and receptor-mediated transfection (Wu and Wu, J. Biol. Chem., 262:4429–4432, 1987; Wu and Wu, Biochemistry, 27:887–892, 1988). (Articles cited in this paragraph are herein incorporated by reference.)

Once the construct has been delivered into the cell the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. The addition of DNA to cationic liposomes causes a topological transition from liposomes to optically birefringent liquid-crystalline condensed globules. These DNA-lipid complexes are potential non-viral vectors for use in gene therapy.

Liposome-mediated nucleic acid delivery and expression of foreign DNA in vitro has been very successful. Using the β-lactamase gene, Wong et al., Gene, 10:87–94, 1980, demonstrated the feasibility of liposome-mediated delivery and expression of foreign DNA in cultured chick embryo, HeLa, and hepatoma cells. Nicolau et al., (Methods Enzymol., 149:157–176, 1987, herein incorporated by reference) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA. In other embodiments, the liposome may be complexed or employed in conjunction with nuclear nonhistone chromosomal proteins (HMG-1). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type specific distribution of various receptors, the delivery can be highly specific (Wu and Wu, Adv. Drug Delivery Rev., 12:159–167, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, J. Biol. Chem., 262:4429–4432, 1987) and transferrin (Wagner et al., Proc. Natl. Acad. Sci. 87(9):3410–3414, 1990). Recently, a synthetic neoglycoprotein, which recognizes the same receptor as ASOR, has been used as a gene delivery vehicle (Ferkol et al., FASEB J., 7:1081–1091, 1993; Perales et al., Proc. Natl. Acad Sci USA, 91:4086–4.090, 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. Methods Enzymol., 149:157–176, 1987, employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor cells, by any number of receptor-ligand systems with or without liposomes. For example, the human prostate-specific antigen (Watt et al., Proc. Natl. Acad. Sci., 83(2):3166–3170, 1986) maybe used as the receptor for mediated delivery of a nucleic acid in prostate tissue.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. Dubensky et al. (Proc. Nat. Acad. Sci. USA, 81:7529–7533, 1984), successfully injected polyomavirus DNA in the form of $CaPO_4$ precipitates into liver and spleen of adult and newborn mice demonstrating active viral replication and acute infection. Benvenisty and Neshif, Proc. Nat. Acad. Sci. USA, 83:9551–9555, 1986, also demonstrated that direct intraperitoneal injection of $CaPO_4$ precipitated plasmids results in expression of the transfected genes. It is envisioned that DNA encoding a CAM may also be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., Nature, 327:70–73, 1987, herein incorporated by reference).

Several devices for accelerating small particles have been developed. One such device relies on a high voltage discharge to generate an electrical current, which in turn provides the motive force (Yang et al., Proc. Natl. Acad. Sci. USA, 87:95689572, 1990). The microprojectiles used have consisted of biologically inert i substances such as tungsten or gold beads.

B. Viral Vector-Mediated Transfer

Another method of achieving gene transfer is via viral transduction using infectious viral particles as a delivery vehicle, for example, by transformation with an adenovirus vector of the present invention as described herein below. Alternatively, retroviral or bovine papilloma virus may be employed, both of which permit permanent transformation of a host cell with a gene(s) of interest. Thus, in one example, viral infection of cells is used in order to deliver therapeutically significant genes to a cell. Typically, the virus simply will be exposed to the appropriate host cell under physiologic conditions, permitting uptake of the virus. Though adenovirus is exemplified, the present methods may be advantageously employed with other viral vectors, as discussed below. Such methods will be familiar to those of ordinary skill in the art.

a) Adenovirus

Adenovirus is particularly suitable for use as a gene transfer vector because of its mid-sized DNA genome, ease of manipulation, high titer, wide target-cell range, and high infectivity. The roughly 36 kB viral genome is bounded by 100200 base pair (bp) inverted terminal repeats (ITR), in which are contained cisacting elements necessary for viral DNA replication and packaging. The early (E) and late (L) regions of the genome that contain different transcription units are divided by the onset of viral DNA replication.

The E1 region (EIA and E 1 B) encodes proteins responsible for the regulation of transcription of the viral genome and a few cellular genes. The expression of the EZ region (E2A and E213) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present invention, it is possible to achieve both these goals while retaining the ability to manipulate the therapeutic constructs with relative ease.

The large displacement of DNA is possible because the cis elements required for viral DNA replication all are localized in the inverted terminal repeats (ITR) (100–200 bp) at either end of the linear viral genome. Plasmids containing ITR's can replicate in the presence of a non-defective adenovirus. Therefore, inclusion of these elements in an adenoviral vector should permit replication.

In addition, the packaging signal for viral encapsulation is localized between 194–385 by (0.5–1.1 map units) at the left end of the viral genome. This signal mimics the protein recognition site in bacteriophage DNA where a specific sequence close to the left end, but outside the cohesive end sequence, mediates the binding to proteins that are required for insertion of the DNA into the head structure. E1 substitution vectors of Ad have demonstrated that a 450 bp (0–1.25 map units) fragment at the left end of the viral genome could direct packaging in 293 cells.

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication deficient vectors, however, since the presence of helper virus, needed to provide replicative functions, would contaminate any preparation. Thus, an additional element was needed that would add specificity to the replication and/or packaging of the replication-deficient, vector. That element, as provided for in the present invention, derives from the packaging function of adenovirus.

It has been shown that a packaging signal for adenovirus exists in the left end of the conventional adenovirus map. Later studies showed that a mutant with a deletion in the E1A (194–358 bp) region of the genome grew poorly even in a cell line that complemented the early (E1A) function. When a compensating adenoviral DNA (0–353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ads DNA molecule.

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over, the mutated versions. Given a limiting amount of packaging factor, the virus containing the wild-type signals are packaged selectively when compared to the helpers. If the preference is great enough, stocks approaching homogeneity should be achieved.

b) Retrovirus

The retroviruses are a group of single-stranded RNA viruses characterized by an ability to convert their RNA to double-stranded DNA in infected cells by a process of reverse-transcription. The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed ψ, functions as a signal for packaging of the genome into virions. Two long terminal repeat (LTR) sequences are present at the 5' and 3' ends of the viral genome. These contain strong promoter and enhancer sequences and also are required for integration in the host cell genome.

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and ψ components is constructed. When a recombinant plasmid containing a human cDNA, together with the retroviral LTR and ψ sequences is introduced into this cell, line (by calcium phosphate precipitation for example), the ψ sequence allows the RNA transcript of the recombinant plasmid to be packaged into viral particles, which are then secreted into the culture media. The media containing the recombinant retroviruses is collected, optionally concentrated, and used for gene transfer. Retroviral vectors are able to infect a broad variety of cell types. However, integration and stable expression of many types of retroviruses require the division of host cells.

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., Proc. Natl. Acad. Sci. USA, 86:9079–9083, 1989). Using antibodies against major histocompatibility complex class I and class II antigens, the infection of a variety of human cells that bore those surface antigens was demonstrated with an ecotropic virus in vitro.

c) Adeno-Associated Virus

AAV utilizes a linear, single-stranded DNA of about 4700 base pairs. Inverted terminal repeats flank the genome. Two genes are present within the genome, giving rise to a number of distinct gene products. The first, the cap gene, S produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

AAV is not associated with any pathological state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector can be obtained by restriction endonuclease digestion of AAV or a plasmid such as psub201, which contains a modified AAV genome (Samulski et al. J. Virol., 61(10):3096–3101, 1987, herein incorporated by reference), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo.

AAV-mediated efficient gene transfer and expression in the lung has led to clinical trials for the treatment of cystic fibrosis (Carter and Flotte, Ann. N. Y. Acad. Sci., 770:79–90, 1995; Flotte et al., Proc. Natl. Acad. Sci. USA, 90:1061310617, 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., J. Yirol, 70:520–532, 1996; Flotte et al., Proc. Natl. Acad. Sci. USA, 90:10613–10617, 1993; Kaplitt et al., Nat. Genet., 8:148–153, 1994; Kaplitt et al., Arm Thord. Surg., 62:16691676, 1996; Koeberl et al., Proc. Natl. Acad. Sci. USA, 94:1426–1431, 1997; McCown et al., Brain Res., 713:99–107, 1996; Ping et al., Microcirculation, 3:225–228, 1996; Mao et al., J. ViroL, 70:8098–8108, 1996).

d) Other Viral Vectors

Other viral vectors may be employed as expression constructs in the present invention. Vectors derived from viruses such as vaccinia viruses (Ridgeway, In: Vectors: A survey of molecular cloning vectors and their uses, Rodriguez R L, Denhardt D T. ed., Stoneham: Butterworth, pp. 467–492, 1988; Baichwal and Sugden, In: Gene Transfer, Kucherlapati R, ed., New York, Plenum Press, pp. 117–148, 1986; Coupar et al., Gene, 68:1–10, 1988) canary pox viruses, lentiviruses and herpes viruses may be employed.

7. Cell Targets

The methods and vectors of the present invention may be used to target a wide variety of cells, organs, and tissues within a mammal.

In some embodiments, the expression constructs described herein are used to treat cancer. The cell which is targeted may be either a tumor cell, a cell within a tumor, or a cell near a tumor. The tumor may optionally be in the brain, lung, liver, spleen, kidney, bladder, lymph node, small intestine, pancreas, colon, stomach, breast, endometrium, prostate, testicle, vulva, cervix, ovary, skin, head and neck, esophagus, bone marrow, or blood. One of ordinary skill in the art will be able to readily discern an appropriate therapeutic gene to be expressed in a given tumor type.

In alternative embodiments, a medical condition other than cancer is being treated. For instance, the present invention provides for highly effective protein replacement therapy. In such a case, a specific type of cell, tissue, or organ may be targeted for expression of a protein which is underexpressed in the subject, especially if the activity of the protein is limited to that specific cell type, tissue, or organ. Again, one of ordinary skill in the art will be able to discern which cells are most appropriately targeted.

The expression construct may be introduced into the cell of interest through an in vitro, ex vivo, or in vivo method. Much gene therapy is currently performed ex vivo, since the transfection or transduction of an isolated cell is often more efficient. The choice of method of introduction will be dependent upon the cell type, tissue, or organ being targeted, as well as the particular delivery vehicle chosen. One of ordinary skill in the art can readily navigate such a choice.

Since the expression constructs of the present invention require induction to be active, in many cases the expression construct may be delivered to a larger part of the subject's body than just the cell, tissue, or organ in which expression is desired. Exposure of the subject to the activating conditions which induce expression of the transferred expression constructs can then be limited to achieve specificity of expression. In many cases, this is preferred. For instance, exposure of a subject to radiation therapy is preferably limited to only those areas necessary. Application of hyperthermia will generally also be limited in its range. In other embodiments, the activating conditions may be conditions inherent to the targeted cell itself. For instance, the hypoxic environment of a tumor will trigger expression when the expression construct has an inducible promoter containing a hypoxia-responsive element. In such cases, the resulting expression, will be by its very nature, very localized, even if delivery of the expression construct was not.

8. Pharmaceutical Compositions and Routes of Administration

It is contemplated that the therapeutic compositions of the present invention may be administered, in vitro, ex vivo or in vivo. Thus, it will be desirable to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

The compositions of the present invention comprise an effective amount of the expression construct or a viral vector or liposome carrying the expression construct, dissolved or dispersed in a pharmaceutically acceptable carrier or aqueous medium. Such compositions also can be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients also can be incorporated into the compositions.

Solutions of the active compounds as free base or pharmacologically acceptable salts can be prepared in water suitably mixed with a surfactant, such as hydroxypropylcellulose. Dispersions, also can be prepared in glycerol, liquid polyethylene glycols, and mixtures thereof and in oils. Under ordinary conditions of storage and use, these preparations contain a preservative to prevent the growth of microorganisms.

The therapeutic compositions of the present invention may include classic pharmaceutical preparations for use in therapeutic regimens, including their administration to humans. Administration of therapeutic compositions according to the present invention will be via any common route so long as the target tissue or cell is available via that route. This includes oral, nasal, buccal, rectal, vaginal or topical. Alternatively, administration will be by orthotopic, intradermal subcutaneous, intramuscular, intraperitoneal, or intravenous injection. Such compositions would normally be administered as pharmaceutically acceptable compositions that include physiologically acceptable carriers, buffers or other excipients. For application against tumors, direct intratumoral injection, injection of a resected tumor bed, regional (e.g., lymphatic) or systemic administration is contemplated. It also may be desired to perform continuous perfusion over hours or days via a catheter to a disease site, e.g., a tumor or tumor site.

The therapeutic compositions of the present invention are administered advantageously in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain about 100 mg of human serum albumin per milliliter of phosphate buffered saline. Other pharmaceutically acceptable carriers include aqueous solutions, non-toxic excipients, including salts, preservatives, buffers and the like may be used. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components of the pharmaceutical composition are adjusted according to well known parameters.

Additional formulations which are suitable for oral administration also are contemplated. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal, for example (i) inhibition of tumor cell proliferation, (ii) elimination or killing of tumor cells, or (iii) gene transfer for short- or long-term expression of a therapeutic gene. The term "unit dose" refers to physically discrete units suitable for use in a subject, each unit containing a predetermined quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the result desired. Multiple gene therapeutic regimens are contemplated by the present inventors.

In one embodiment, a vector encoding a therapeutic gene is used to treat cancer patients. Typical amounts of a viral vector used in gene therapy of cancer is $10^{6-10^{15}}$ PFU/dose (e.g., $10^6$ $10^7$, $10^8$, $10^9$, $10^{10}$, $10^{11}$, $10^{12}$, $10^{13}$, $10^{14}$ and $10^{15}$) wherein the dose is divided into several injections at different sites within a solid tumor. The treatment regimen also involves several cycles of administration of the gene transfer vector over a period of 3–10 wk. Administration of the vector for longer periods of time from months to years may be necessary for continual therapeutic benefit.

In another embodiment of the present invention, a viral vector encoding a therapeutic gene may be used to vaccinate humans or other mammals. Typically, an amount of virus effective to produce the desired effect, in this case vaccination, would be administered to a human or other mammal so that long term expression of the transgene is achieved and a host immune response develops. It is contemplated that a series of injections, for example, a primary injection followed by two booster injections, would be sufficient to induce a long term immune response. A typical dose would be from $10^6$ to $10^{15}$ PFU/injection depending on the desired result. Low doses of antigen generally induce a strong cell-mediated response, whereas high doses of antigen generally induce an antibody-mediated immune response. Precise amounts of the therapeutic composition also depend on the judgment of the practitioner and are peculiar to each individual.

EXAMPLES

The following specific examples are intended to illustrate the invention and should not be construed as limiting the scope of the claims.

Example 1

The Heat Shock Promoter Can Induce Expression of a Reporter Gene

Vector Constructs. To study the ability of the HSP70 promoter to induce gene expression, either a minimal heat shock (HS) promoter or a minimal CMV promoter was inserted upstream of a reporter gene in a plasmid containing neomycin and ampicillin selectable markers. The basic design of a plasmid (M5) containing one multiple cloning site in operable position to a promoter derived from HSP70 is shown in FIG. 1. M5 was constructed by replacing the CMV promoter in pcDNA3.0 (Invitrogen, Inc.) with a minimal HSP70B promoter (SEQ ID NO: 1, FIG. 10), a 0.4 kb fragment (HindIII-BamHI) of the human heat shock protein 70B (HSP70B) promoter, obtained from StressGen, Inc.

Activity of the minimal HS and CMV promoters were determined by transfecting human cancer cells, MCF7 human breast carcinoma cells and DU 145 human prostate carcinoma cells, with the plasmid S8. The S8 plasmid, derived from the M5 vector of FIG. 1, contains the minimal HSP70B promoter operably linked to the gene encoding Enhanced Green Fluorescence Protein (EGFP). S8 was constructed by inserting the EGFP gene from pEGFP-1 (Clonetech, Inc.) into the multiple cloning site (MCS) of M5.

Cell Culture and Transfection. Human DU-145 prostate cancer derived cells and MCF-7 human breast cancer derived cells were transfected with the S8 vector described above. To isolate cells stably transfected with S8, cultures were transfected using standard calcium phosphate precipitation methods. Cells containing the integrated plasmids were selected for their ability to proliferate in the presence of neomycin. Heat shock was administered by completely submersing culture flasks in a temperature controlled ($\pm 0.1°$ C.) waterbath.

One positive clone, clone 4, and a polyclonal line were selected with geneticin from the MCF7 cells' transfection. One polyclonal line was selected with geneticin from the DU-145 cell's transfection. (In each case, the cells were selected with geneticin for 2 weeks.) The selected lines were then analyzed and sorted by FACS.

Isolation of Positive Cell Lines. Cells expressing high levels of EGFP in response to heat shock were selected both using conventional serial dilution methods and by fluorescence activated cell sorting (FACS) methods. Expression of EGFP was quantitated using flow cytometry. The Enhanced Green Fluorescence Protein (EGFP) excites at 490 run allowing it to be viewed under a fluorescence microscope or analyzed by FACS. Cells expressing EGFP were sorted from cells not expressing EGFP by using the FACS method. This was done with Geneticin-selected cell lines. The reason that this is required is that in a polyclonal cell line there are populations that have the S8 plasmid integrated in a way that interferes with the expression of the reporter gene. By sorting the cells these populations can be removed leaving the purely positive population for further analysis.

Figure 2:
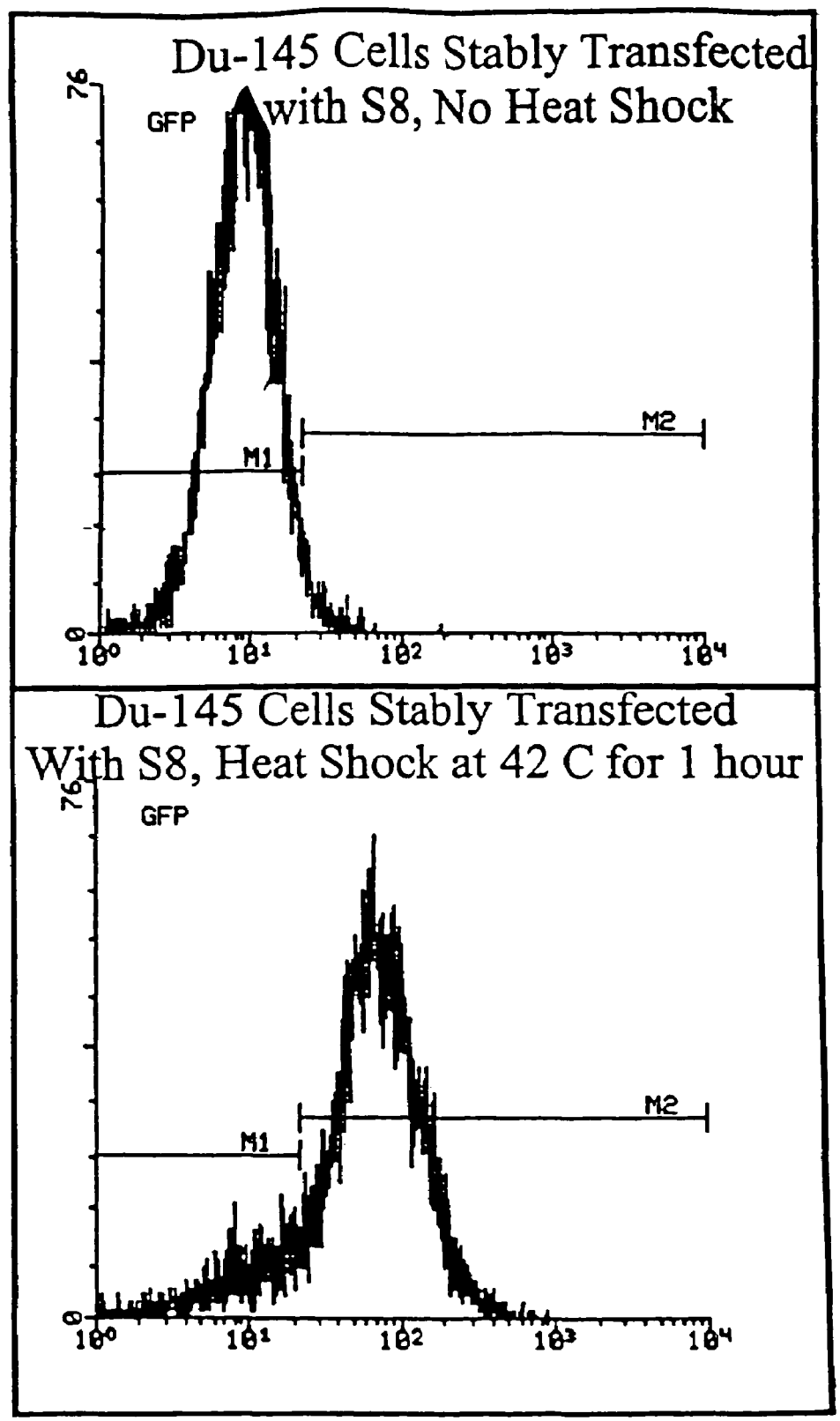
FIG. 2 shows fluorescence activated cell sorting (FACS) histograms for DU-145 cells stably transfected with the S8 plasmid. Fluorescence increases from left to right. The top histogram is from transfected DU-145 cells which have not been subjected to heat shock. The bottom histogram is from transfected DU-145 cells which have been subjected to a 42° C. heat shock for 1 hour.
Figure 3:
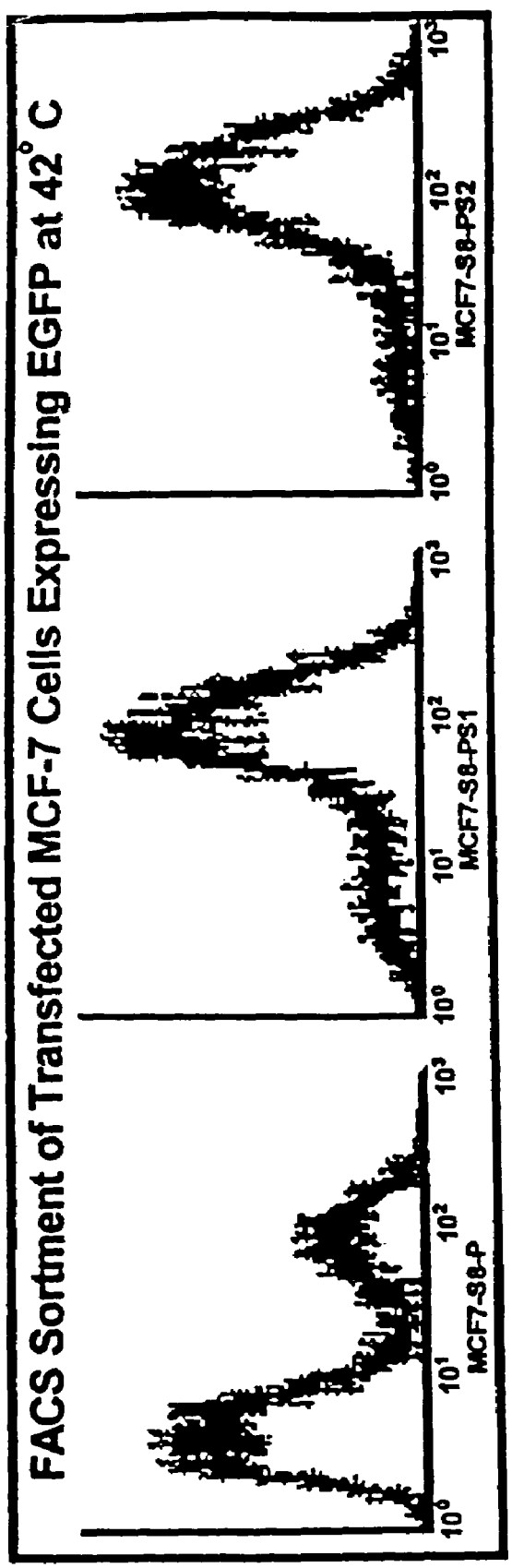
FIG. 3 shows FACS histograms for three different populations of S8 transfected MCF7 cells. The MCF7 cells, transfected with the S8 construct, were sorted by FACS. The original population came from a polyclonal selected cell line. That cell line's activated (i.e., cells expressing EGFP) population was separated from the non-activated population. After the sort, the positive population was grown and then re-sorted to obtain a more purely positive cell line. In this case, the polyclonal MCF7-S8-P cells were sorted twice yielding the highly positive population MCF7-S8-PS2.

As seen in FIG. 2, mean fluorescence from EGFP in DU-145 cells stably transfected with the minimal heat shock promoter driving EGFP(S8) and growing at 37° C. was approximately 10 relative fluorescence units. Four hours after exposure to 42° C. heat shock for one hour, the mean relative fluorescence was 7–9 times greater. Relative gene expression was subsequently quantitated by measuring changes in relative fluorescence in stably transfected cells. The sorting by FACS of MCF7 cells transfected with the S8 plasmid is illustrated in FIG. 3.

Kinetic Studies. Heat exposure survival studies were conducted to evaluate the optimal times/temperatures at which MCF7 cells could by heated without causing massive cell death. For 40° C. and 42° C. up to 1 hour cell death was found to be negligible with less than a 3% cell death. At 44° C. for a time of only 30 minutes almost 50% of the cells had died.

Using the optimal survival times above, initial kinetic studies were performed. Heating transfected MCF7 cells for 1 hour at 40° C. and 42° C. produced more EGFP than heating for only 30 minutes when assayed by FACS. The optimal recovery time for the, cells after heating was 4 hour. Any additional recovery time did not increase the levels of EGFP. For heat treatments done at 44° C. for 30 min, the recovery time took longer with 8 hours being maximal.

EGFP Expression at 37° C.–44° C. in Various Cell Lines. The following heating/recovering times were used as identified in the kinetic studies for testing the inducibility of EGFP driven by the HSP70-derived promoter in all of the inventors' transfected cell lines:

40° C.—1 h of heat treatment, 4 h of recovery
42° C.—1 h of heat treatment, 4 h of recovery
44° C.—30 min of heat treatment, 8 h of recovery Using these temperatures/times the following cell lines were tested for EGFP expression:

MCF7: breast carcinoma parental cell line.
Du145: prostate carcinoma parental cell line.
MCF7-S8-P: MCF7 cells transfected with the S8 plasmid, polyclonal line.
MCF7-S8-PS1: MCF7-S8-P cells that were sorted for EGFP expression by FACS once.
MCF7-S8-PS2:MCF7-S8-PS 1 cells that were resorted for EGFP expression by FACS.
MCF7-S8-4: Clone 4 of the MCF7 S8 transfection.
MCF7-S8-4S1: MCF7-S8-4 cells sorted once for EGFP expression.
Du145-S8-P: Du145 cells transfected with the S8 plasmid, polyclonal line.

Figure 4:
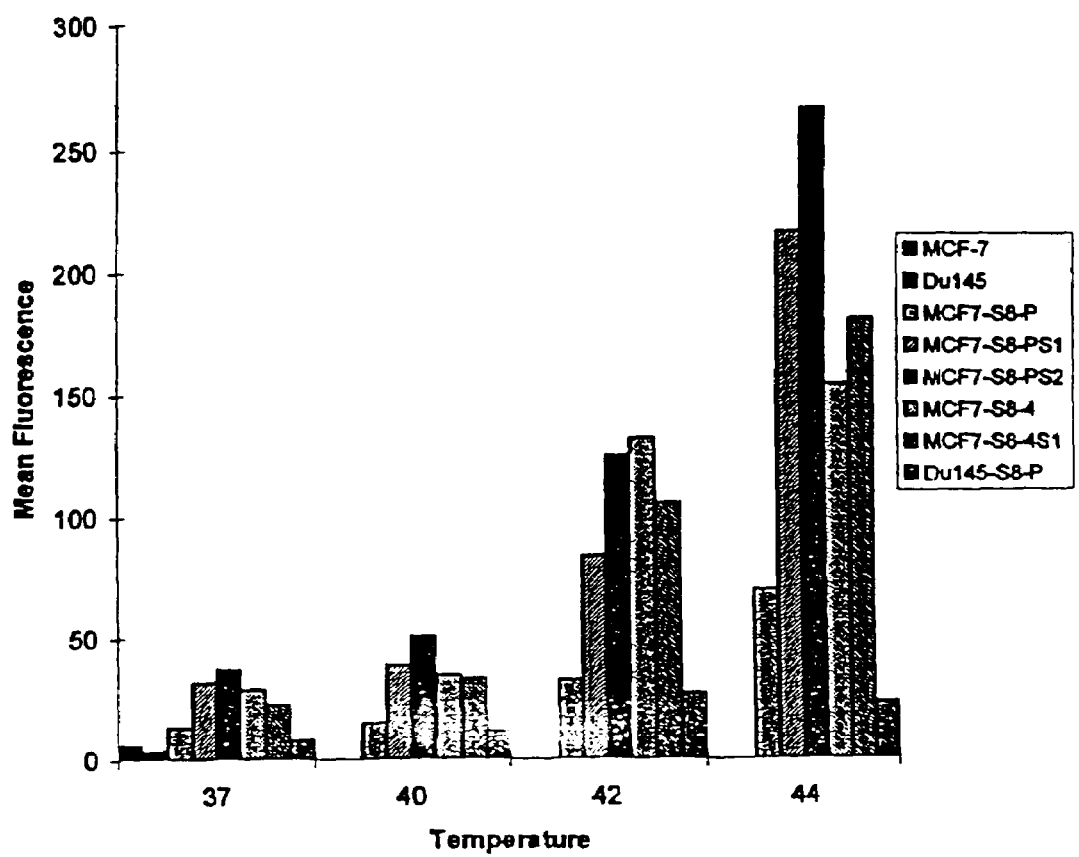
FIG. 4 shows expression of EGFP in different cell lines assayed by FACS. Cell lines were transfected with the plasmid S8. The cells were then cloned or a polyclonal line was grown. In some cases the cell lines were sorted for EGFP expression by FRCS. The total mean fluorescence was quantified and graphed.

The expression seen from the transfected lines of EGFP driven by the HSP70-derived promoter is shown in FIG. 4. As the temperature increases the relative amount of EGFP also increases. These data show that the inventors' heat shock promoter does indeed respond to heat. However, at 37° C. there was still expression of EGFP.

Figure 5:
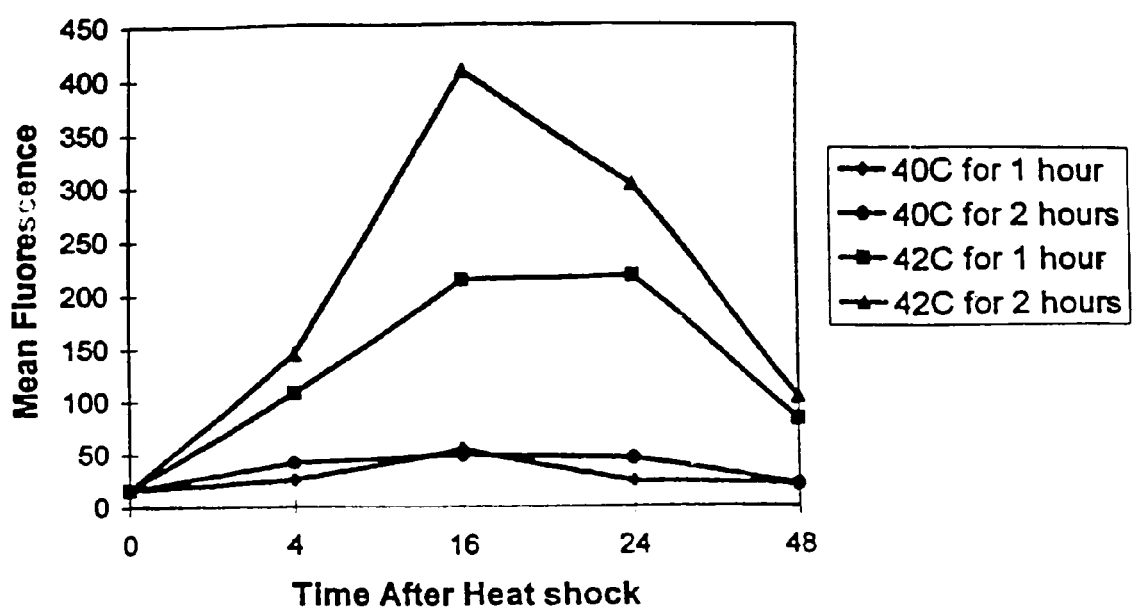
FIG. 5 shows expression of EGFP in stably transfected DU-145 cells which have been twice sorted (DU-S8-PS2) following heat shock. The DU-S8-PS2 cells were heated at either 40° C. or 42° C. and allowed to recover for various times. The cells were then analyzed by FACS.

EGFP Expression in Stably Transfected DU-145 Cells. After Heat Shock. The induction of endogenous heat shock promoters is transient and temperature dependent. When DU-145 cells, stably transfected with the minimal HS promoter driving EGFP expression (S8) and selected twice by FACS (DU-S8PS2 cells), were heat shocked for various times and at various temperatures, reporter gene expression was temperature-dependent and expression was transient with maximal values at 15–24 hours after the inducing stress (FIG. 5). These results indicate that the promoter is transiently activated under the conditions used here and that EGFP is unstable, since fluorescence decreases after 15–24 hours in these cells. The minimal heat shock promoter activity increases transiently by approximately 3 fold after a 40° C. heat shock for either 1 or 2 hours. Promoter activity increases 13 and 25 fold after 42° C. heat shock for either 1 or 2 hours, respectively.

Figure 6:
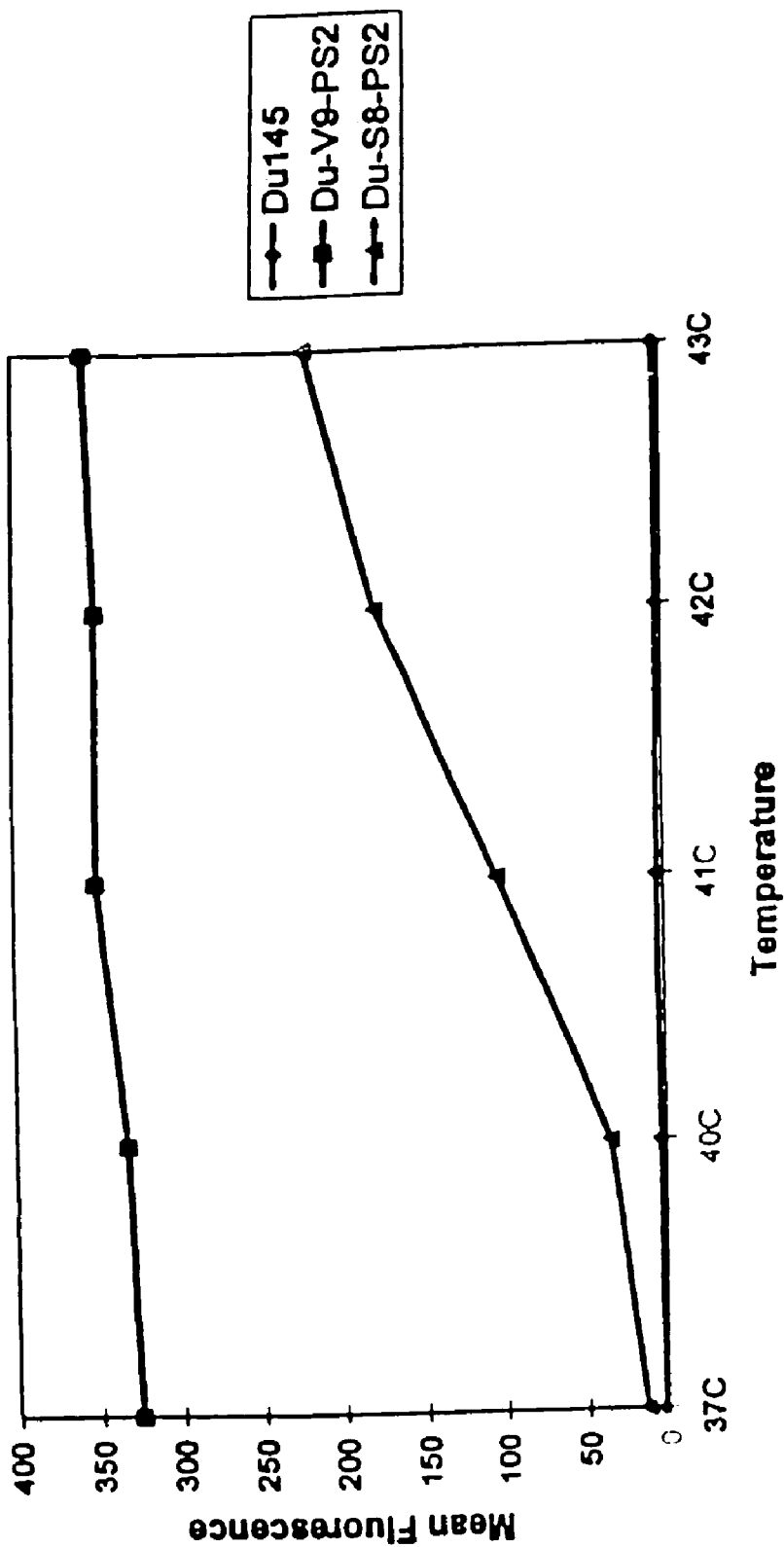
FIG. 6 shows expression levels of EGFP in stably transfected DU-145 cells 16 hours after exposure to heat stresses. One population of cells (DU-S8-PS2) was stably transfected with the S8 plasmid. Another population (DU-V9-PS2) was stably transfected with the V9 plasmid, a plasmid identical to S8 except that the EGFP of the V9 plasmid is operably linked to a CMV promoter, rather than HSP 70B (see FIG. 7). The cells were heated at various temperatures and allowed to recover for 16 hours. Non-transfected DU-145 cells were included as a control.
Figure 7:
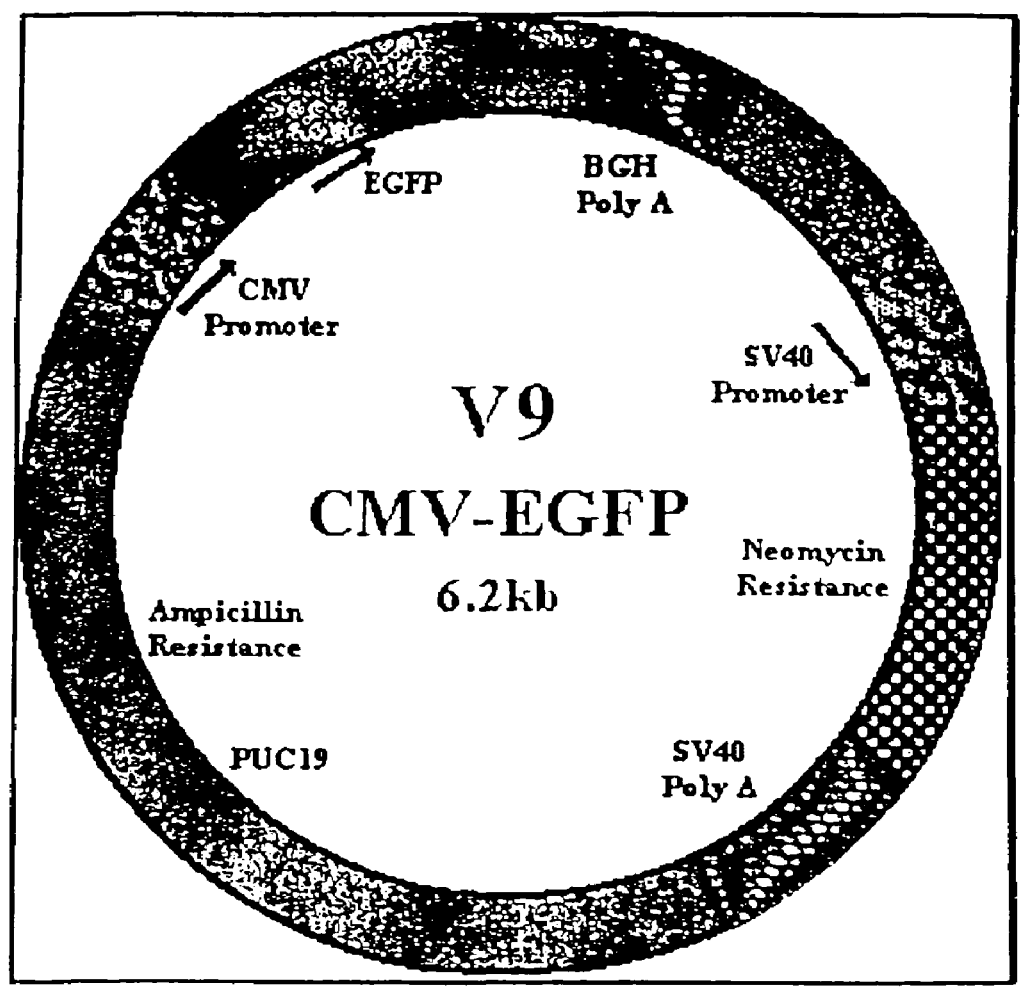
FIG. 7 shows a schematic diagram of the plasmid V9 which contains a CMV promoter that is operably linked to the gene encoding the Enhanced Green Fluorescence Protein (EGFP)

Comparison of Expression of EGFP Under Control of Heat Shock and CMV Promoters. The data presented in FIG. 6 show that minimal heat shock promoter activity in DU-S8-PS2 cells is temperature-dependent over the range from 37–43° C. In contrast, DU-145 cells stably transfected with V9, a vector in which the CMV promoter drives EGFP expression (FIG. 7), express nearly 50% higher levels of promoter activity than do these same cells transfected with the minimal heat shock promoter and induced with 43° C. heat shock. The CMV promoter activity is essentially unaffected by temperature in these cells. The temperature-dependence of the minimal HS promoter is not specific to the DU-145 cells.

Example 2

Figure 9A:
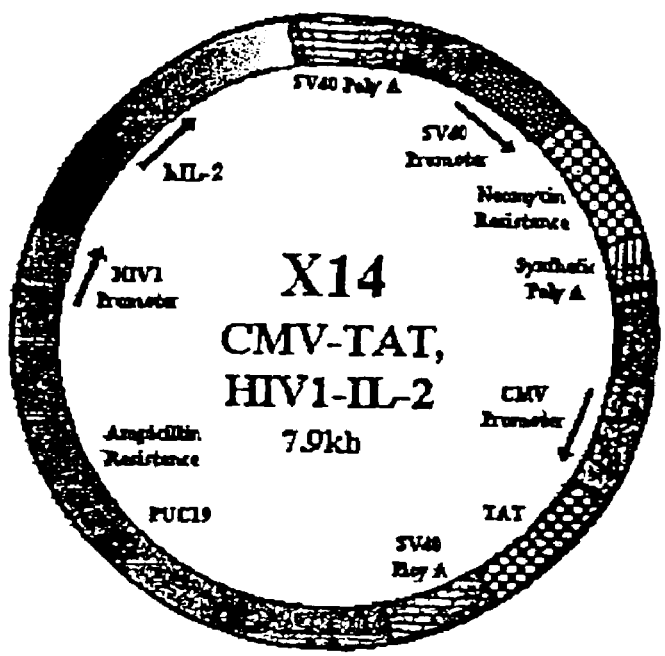
FIG. 9A shows—a plasmid designated X14 containing a CMV-TAT-HIV 1-IL2 expression cassette.
Figure 9B:
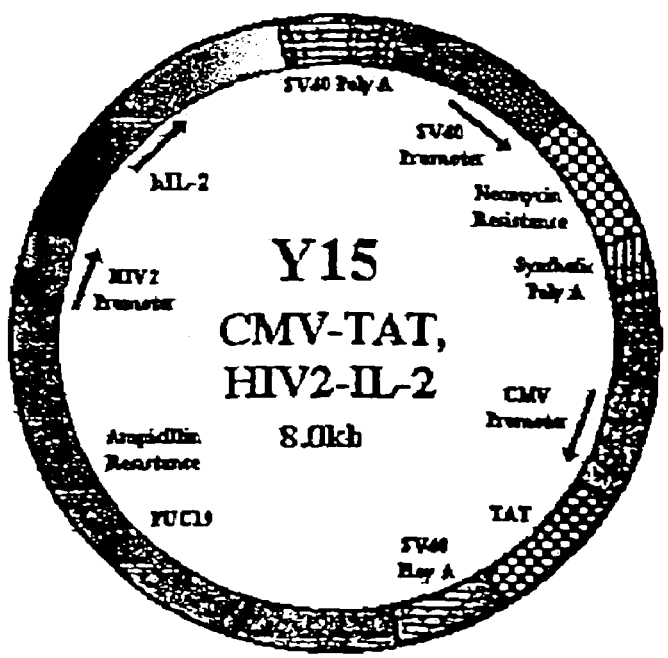
FIG. 9B shows a plasmid designated Y15 containing a CMV-TAT-HIV-2-IL2 expression cassette.
Figure 9C:
FIG. 9C shows a plasmid designated pf12 containing an HSP-TAT-HIV-1-IL2 expression cassette.
Figure 9D:
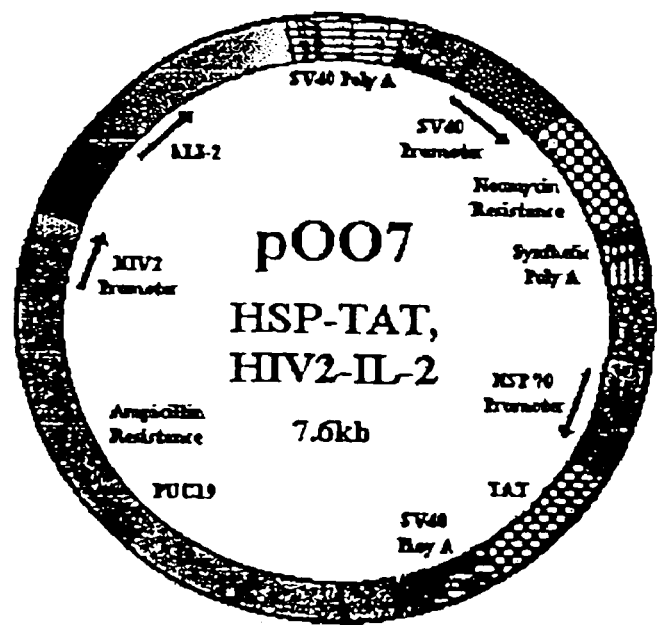
FIG. 9D shows a plasmid designated p007 containing an HSP-TAT-HIV-2-IL2 expression cassette.

Expression of IL-2 can be Amplified by the Use of a HIV Promoter and Tat in a Construct Initial Amplifier Studies. Studies involving new constructs capable of amplifying a therapeutic gene's expression were performed. To demonstrate the principle of the amplifier idea, several constructs were produced. The constructs contain a constitutive promoter, the CMV promoter, rather than a heat shock induble promoter. These constructs are the plasmids L-27, X14, RR13, Y15, and SS 10. Table 3, below, shows the promoters/genes present in each plasmid and the amount of IL-2 produced. Four of the plasmids were obtained from a plasmid containing two multiple cloning sites. In these four plasmids, the CMV promoter was inserted upstream of either the tat gene or a multiple cloning site (MCS) and either the HIV I or HIV2 long terminal repeats (LTRs) was inserted upstream of the mouse interleukin-2 (IL-2) gene. The plasmids X14 and Y15 are shown schematically in FIGS. 9A and 9B. The L-27 plasmid served as a reference. IL-2 was measured from tissue culture supernatants by ELISA using the IL-2 EASIA kit (Medgenix Diagnostics, Fleurus, Belgium). The sensitivity of the kit is estimated 10 at O.1 IU IL-2/ml. In this study, SW480 cells were transfected with the lipid Dosper (see the transfection protocol of Example 3, below.).

TABLE 3

| Plasmid Name | Promoter/gene | Amount of IL-2 in I.U. |
|---|---|---|
| Lipid alone | Dosper | .48 |
| L-27 | CMV/IL-2 | 15.63 |
| RR13 | HIV/IL-2 CMV/multiple cloning site | 17.56 |
| X14 | HIV1/IL-2 CMV/TAT | 173.7 |
| SS10 | HIV2/IL-2 CMV/multiple cloning site | 12.83 |
| Y15 | HIV2/IL-2 CMV/TAT | 440.55 |

It can be seen from this study that the complete amplifier constructs are capable of increased expression over the CMV promoter. Also, the production of the transactivating factor, TAT, is required for this increased production.

Example 3

Heat Inducible Amplifiers

Figure 8:
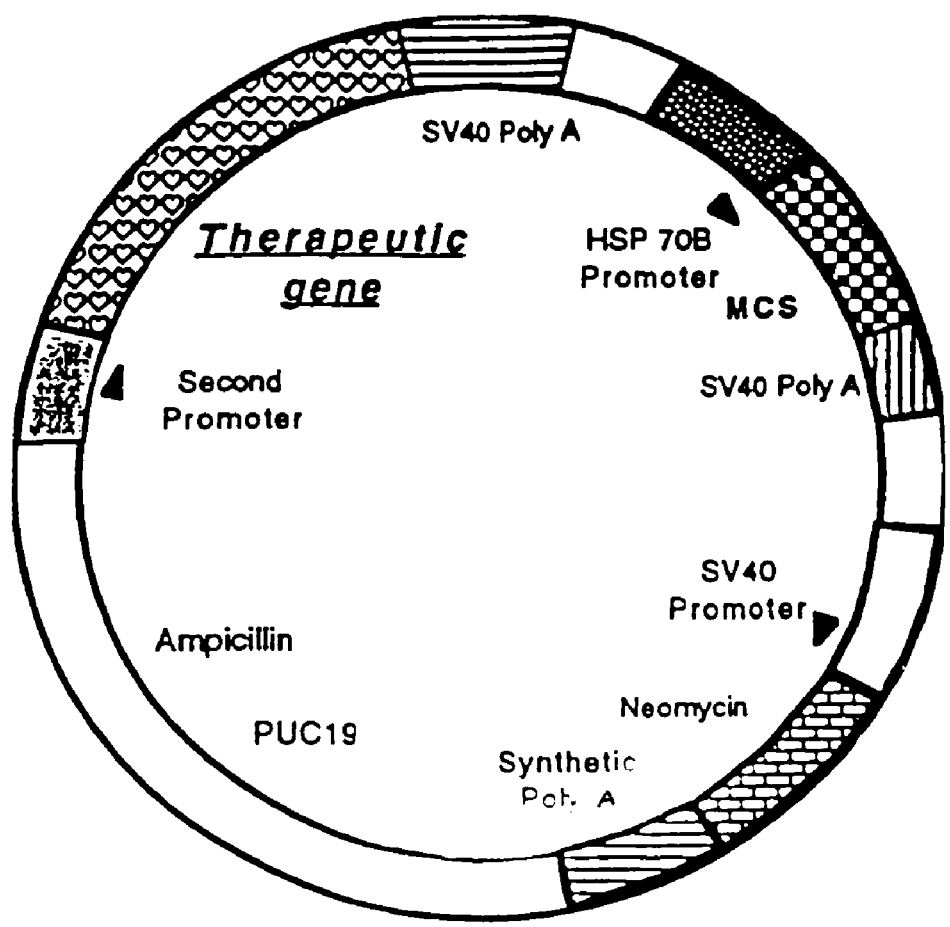
FIG. 8 shows the basic vector design for a vector containing a second promoter which allows for amplification of the heat shock response. The plasmid contains a multiple cloning site (MCS) operably linked to HSP70B promoter, but also contains a therapeutic gene operably linked to a second promoter. The plasmid also contain the neomycin resistance gene, the ampicillin resistance gene, and standard elements for growth in bacteria. In the plasmid pC8, the second promoter is the HIV-1 long terminal repeat (LTR) and the therapeutic gene is IL2. In pf12, tat is inserted in the MCS, the second promoter is the HIV-1 LTR, and the therapeutic gene is IL2. Another plasmid, p007, is the same as pf12, except that the HIV-2 LTR is used as the second promoter.

Vector Construction. To determine if a second promoter could be used to increase the activity of the minimal. HS promoter, MCF-7 cells were transiently transfected with a series of vectors, including pC8, pf12, and p007 (FIGS. 8 and 9). Using a plasmid containing two multiple cloning sites, the minimal heat shock promoter was inserted upstream of either the tat gene or a multiple cloning site (MCS) and either the HIV 1 or HIV2 long terminal repeats (LTRs) was inserted upstream of the mouse interleukin-2 (IL-2) gene. The plasmids also each carried neomycin and ampicillin selectable markers.

The plasmid f11 was first created by inserting a 0.5 kb EcoRI fragment, containing the interleukin-2 (IL-2) coding region (see GenBank accession no. 577834), from plasmid C5 into the ECOR1 site of the vector M5 (see specific example, Example 1, above). The plasmid C8 was constructed by inserting a 1 kb BamHI fragment, containing the 0.4 kb HSP70B fragment upstream of a MCS from plasmid B4527 (see Tsang, et al., Biotechniques 20:51–52, 1996 and Tsang et al., Biotechniques 22:68, 1997, both herein incorporated by reference), into the BamHI site of plasmid DNP-1 (Tsang et al., 1996, and Tsang et al., 1997), which contains the HIVI LTR upstream of the IL-2 coding region. The vector f12 (FIG. 9) was then constructed by inserting a 0.4 kb NotI fragment, containing the coding region for the HIV tat gene, into the NotI site of C8. An intermediate vector D10 was constructed by inserting the 1 kb BamH I fragment containing the minimal HSP70B promoter into plasmid MNP-7 (Tsang et al., 1996, and Tsang et al., 1997), which contains the HIV2 LTR upstream of the IL-2 coding region. Plasmid 007 (FIG. 9) was created by inserting the 0.4 kb Not I fragment, encoding the tat gene, into the Not I site of D10.

Transfection Protocol. Transfections were performed, according to the published procedure (Stopeck, et al., Cancer Gene Therapy, 5:119–126, 1998.) MCF-7 cells were plated in either a 6 well or 12 well plates. The next day, cells were washed with Hanks Buffered Saline Solution and replaced with a 1 ml transfection solution. The transfection solution was a 4:1 lipid to DNA mass ratio of either Dosper (1,3-Di-Oleoyloxy-2-(6-Carboxy-sperrnyl)-propylamid, from Boehringer Mannheim) or Dmrie C (1,2-dimyristyloxypropyl- 3dimethyl-hydroxy ethyl ammonium bromide, from Gibco BRL) with either 1.25 µg or 2.5 µg of plasmid DNA in serum-free OptiMEM (from Gibco BRL). Fetal bovine serum (FBS) was immediately added to each well to a final concentration of 10% (vol/vol). Dmrie C was determined to be a better lipid then Dosper. Cells were incubated for 24 hours before heating and 24 hours after heating prior to IL-2 quantitation.

Heat-Induced Amplification Studies. In one set of experiments, cells transfected with the pC8, pf12, or p007 plasmids were assayed for IL-2 expression activity. IL-2 was measured from tissue culture supernatants by ELISA using the IL-2 EASIA kit (Medgenix Diagnostics, Fleurus, Belgium). The sensitivity of the kit is estimated at 0.IIU IL-2/ml. The data from this set of experiments are shown in Table 4, below. This table shows IL-2 expression levels in MCF7 cells which were transfected with Dosper, heated 24 hours later, and were then assayed by ELISA 49 hours after the transfection. The plasmids L-27 (a plasmid used for reference that expresses IL-2 driven by the CMV promoter), 007, f12, and C8 were all tested.

TABLE 4

| temperature heat shock duration: | 37° C. continuous | 39° C. continuous | 41° C. 1 hr | 42° C. 1 hr | 44° C. 0.5 hr |
|---|---|---|---|---|---|
| | | | I.U. of IL-2 | | |
| Lipid alone | 2.03 | 0.50 | 0.41 | 0.53 | 0.53 |
| L-27 | 14.28 | 9.88 | 5.95 | 9.88 | 7.80 |
| 007 | 336.76 | 318.49 | 334.02 | 373.74 | 389.27 |
| F12 | 8.40 | 6.88 | 49.93 | 60.02 | 88.13 |
| C8 | 9.19 | 8.03 | 11.74 | 8.73 | 16.37 |

From this study it can be seen that pf12 is responsive to heating and produces larger quantities of the heat shock amplifier construct IL-2 than either pC8 or pL-27 does. At 37° C., pf12 produced 5-fold more IL-2 than its CMV driven control, L-27. When cells were heat shocked at 39° C. overnight, pf12 produced 7-fold more IL-2 than the CMV driven controls at 37° C. A 1 hour heat shock treatment at 41° C. or 42° C. increased expression from the amplifier constructs by as much as 26-fold, compared to the CMV-driven control vector at 37° C. (However, the p007 plasmid at 37° C. is already near its maximal activity and does not increase expression levels greatly with heat.) The activity of pf12 is also at a high level at 37° C. These results showed that the amplifier strategy can augment the levels of gene expression at temperatures between about 37° C. and about 42° C.

In a different set of experiments, variations in transfection efficiencies were accounted for by co-transfection with a control plasmid in which the CMV promoter was upstream of P-galactosidase. The general protocol for these experiments was to transfect cells 24 hours after subculture, heat shock cultures an additional 24 hours later, change culture medium and then collect medium for measurement of IL-2 levels 24 hours later. As seen in Table 5, below, the activity of the CMV promoter was only minimally affected by heat shock. The minimal heat shock promoter activity was very low in cells maintained at 37° C. and was induced over 20 fold by heat shock at 42° C. As seen in the stably transfected cells, the minimal heat shock promoter activity was only about one half that of the CMV promoter.

TABLE 5

| Vector | Promoter | 37° C. | 42° C.** | Fold (42/37) | Relative*** |
|---|---|---|---|---|---|
| | | Interleukin-2 (IL2) Expression* | | | |
| L27 | CMV-IL2 | 82.67 | 93.4 | 1.1 | 1.0 |
| C8 | HSP-MCS HIV1-IL2 | 84.7 | 70.6 | 0.8 | 1.9 |
| f11 | HSP-IL2 | 2.3 | 54.0 | 23.7 | 0.4 (1) |
| f12 | HSP-TAT HIV1-IL2 | 107.6 | 347.4 | 3.2 | 6.9 (17) |
| 007 | HSP-TAT HIV2-IL2 | 747.5 | 1642.9 | 2.2 | 83.3(208) |

*values in IU IL2 produced per mg cell protein in 24 hours
**heat shock was for 1 hour
***based on 42° C. values and co-transfection with CMV-9-gal The HIV1 promoter, in the absence of tat expression, was similar to that of the CMV promoter and was nearly independent of heat shock. However, when the minimal heat shock promoter was used to express tat, reporter gene expression was dramatically increased after 42° C. heat shock. In cells transiently transfected with heat shock promoter/tat and HIV1/IL-2, IL-2 production was similar to that for heat shock promoter/MCS and HIV1/IL2 in cells maintained at 37° C. This activity was increased over 3 fold, and to levels nearly 7 fold greater than CMV promoter activity by itself, after 42° C. HS.

The HS promoter/tat and HIV2/IL-2 transfected cells showed substantial reporter gene expression in cells maintained at both 37 and after 42° C. heat shock. Relative promoter activity, measured by IL-2 production was over 80 fold higher than that for the CMV promoter alone. Temperature regulation was reduced, with reporter gene expression approximately 2 times higher after 42° C. heat shock compared to the same activity in cells maintained at 37° C.

The temperature dependence of reporter gene expression was not influenced by the presence of a second promoter. As shown in Table 6, below, reporter gene expression, in cells transiently transfected with the minimal heat shock promoter/tat and HIV2/IL-2 containing plasmid, increased in a temperature-dependent manner between 37 and 44° C. These results are qualitatively similar to those seen in FIGS. 4 and 6 for cells stably transfected with only the minimal heat shock promoter.

TABLE 6

| Vector | Promoter | 37° C. | 39° C. | 40° C. | 41° C. | 42° C. | 44° C. |
|---|---|---|---|---|---|---|---|
| | | IL-2 Expression (IU/ml)* | | | | | |
| C8 | HSP-MCS HIV1-IL2 | 7.2 | 9.3 | 6.0 | 4.8 | 5.3 | 7.0 |
| f12 | HSP-TAT HIV1-IL2 | 40.6 | — | — | — | 133.1 | — |
| 007 | HSP-TAT HIV2-IL2 | 224 | 222 | 230 | 250 | 375 | 470 |

MCF7 breast cancer cells were transiently trandected with vectors as shown; heat shocked for 1 hr 24 hrs later; media were collected and IL2 measured 24 hrs after heat shock Example 4

Animal Studies

Mouse models of human cancer, with the histologic features and metastatic potential resembling tumors seen in humans, can be treated with the therapeutic compositions of the present invention. In one embodiment of the present invention, SCID mice are injected with human tumor cells stably transfected with reporter constructs in which the HSP70B promoter is driving the expression of TAT and in which the HIV-1 or HIV-2 promoter is driving either EGFP or IL-2 expression. After growing the tumors to an appropriate measurable size of for example, 1 cm in diameter, the tumors are heated using ultrasound to temperatures up to about 42° C. Gene expression is quantitated at various times after heating by either removing the tumor, making tissue slices and measuring fluorescence from EGFP or measuring tumor tissue levels of IL2 using ELISA. Using another embodiment of the present invention, human tumor cells are injected into SCID mice. The tumors grown to an appropriate measurable size and injected with DNA-lipid complexes. Tumors are heated using ultrasound and gene expression measured at times after heating. The efficacy of these treatments is indicated by a decrease in the size of the tumor, a decrease in metastatic activity, a decrease in cell proliferation or a halt in the tumor growth as a result of the administration of the therapeutic compositions of the present invention.

Example 5

Figure 11:
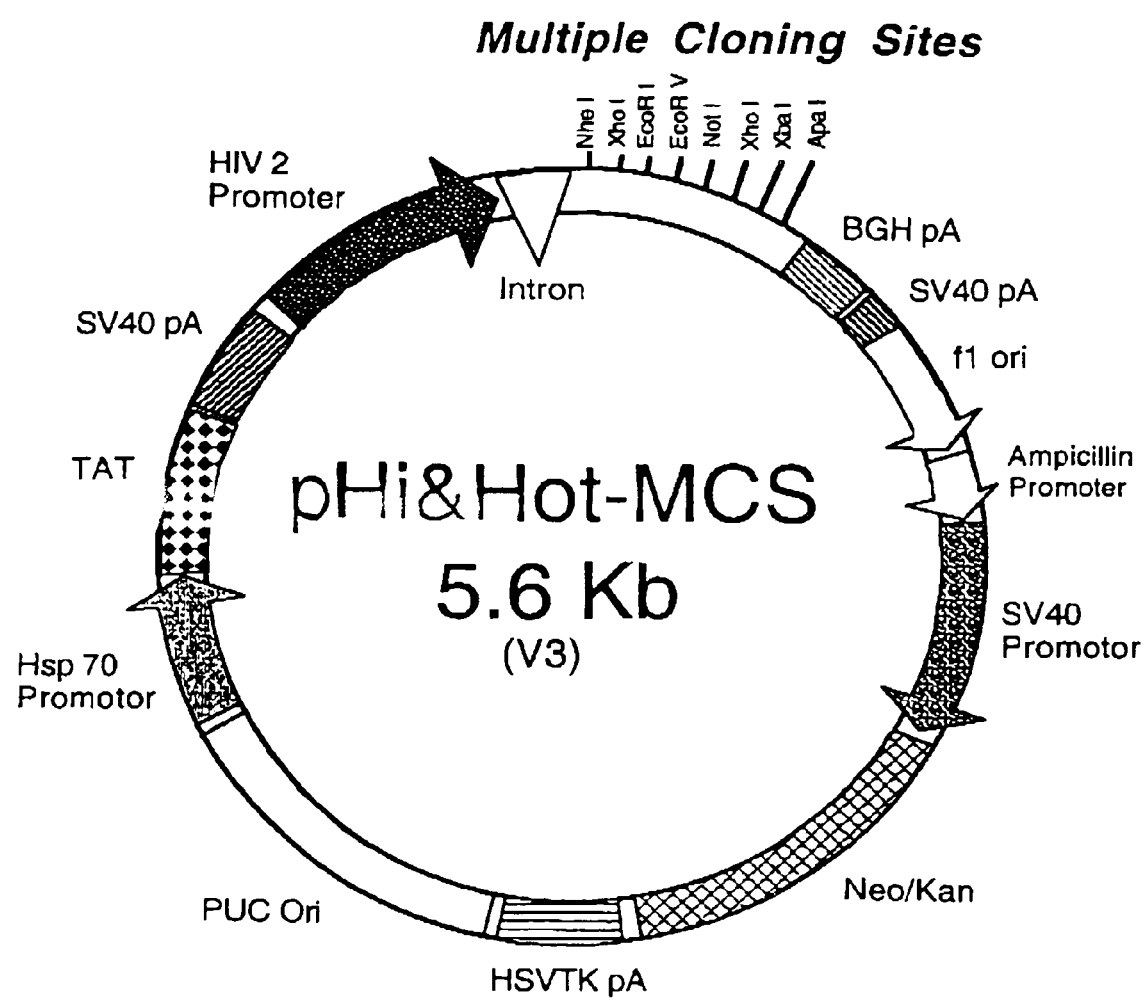
FIG. 11 shows a plasmid designated pHi&Hot-MCS which contains the TAT transcriptional activator under the control of the hsp70 promoter, the HIV2 promoter upstream of a multiple cloning site utilizing a BGH poly A sequence, and a single transcript providing neomycin and kanamycin resistance genes under the control of the SV40 promoter.
Figure 12:
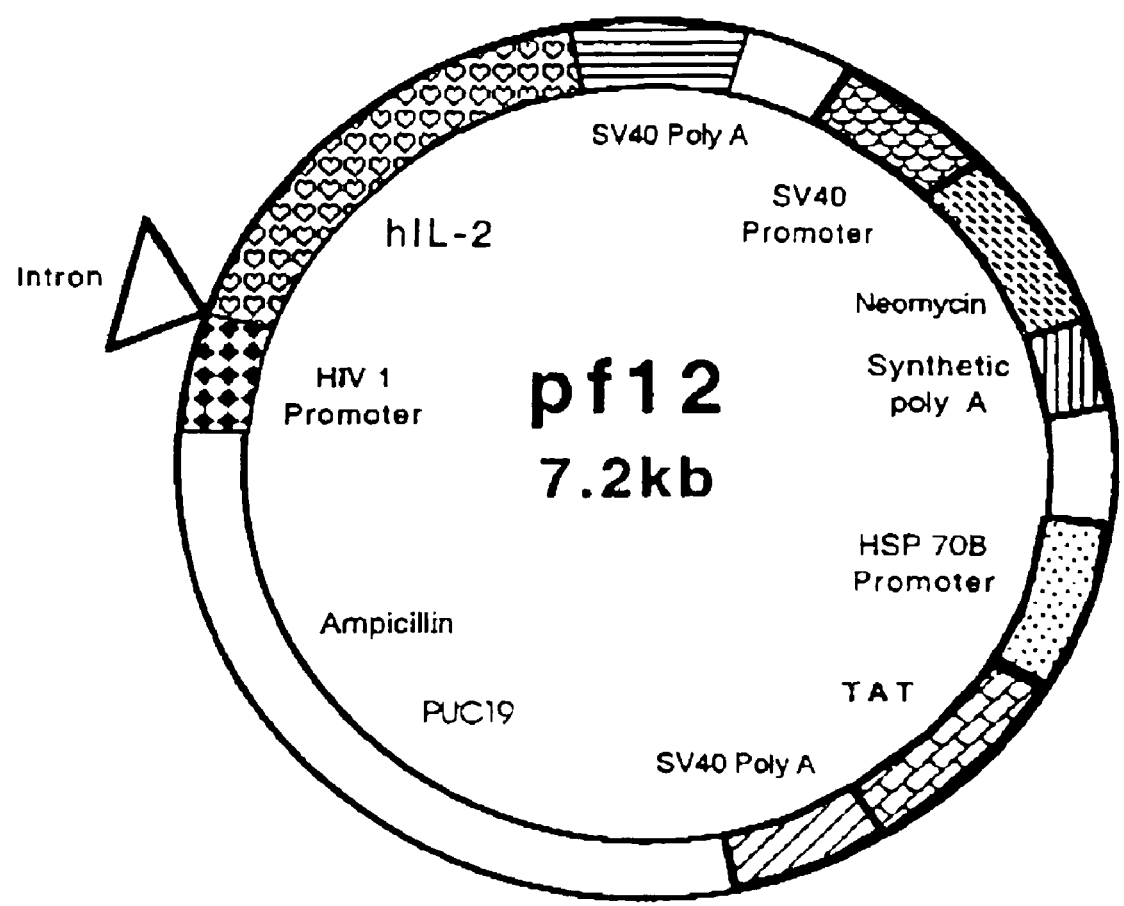
FIG. 12 shows the pf12 vector map.
Figure 13:
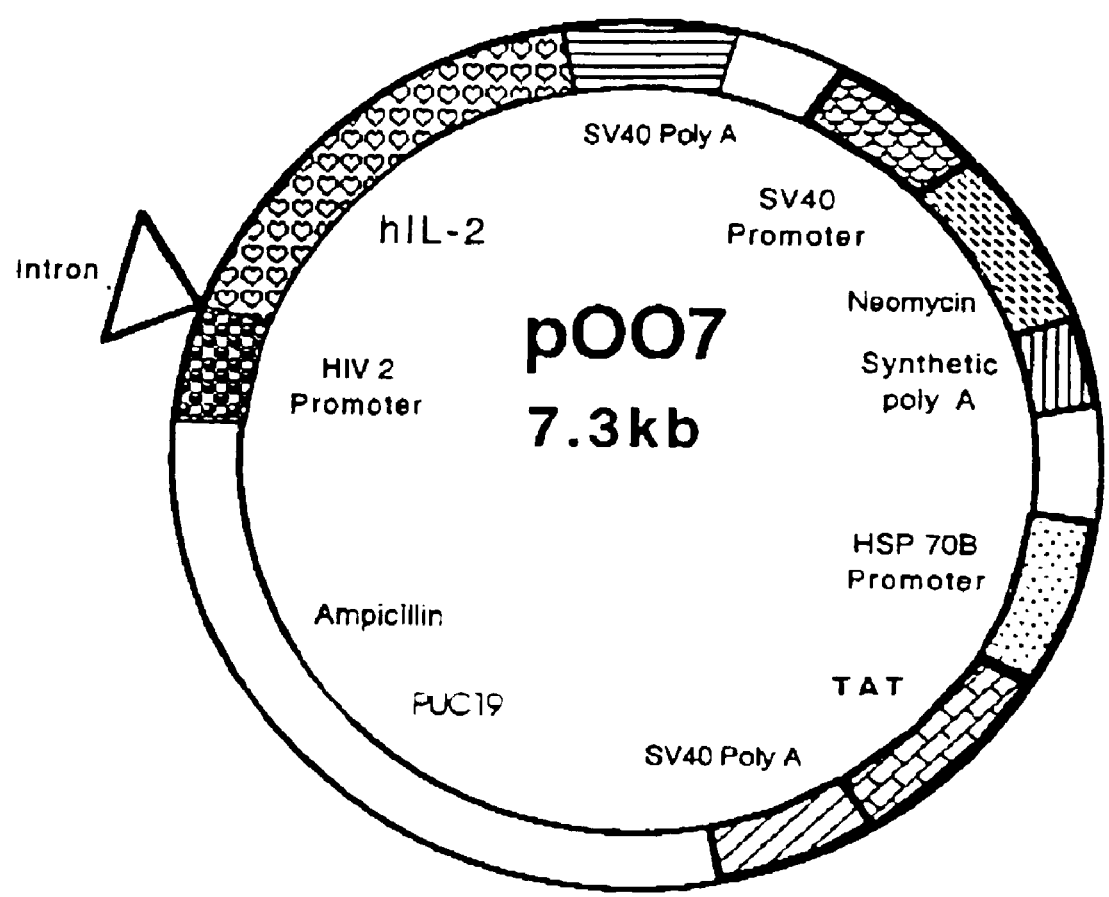
FIG. 13 show the p007 vector map.

A vector construct was prepared to facilitate gene expression induction with heat mediated by the HSP70 promoter. The pHi&Hot-MCS vector shown in FIG. 11 was constructed by assembling DNA fragments from the following sources: HIV1 LTR, HIV2 LTR, IL-2 gene and tat gene were obtained as described in Tsang, T. C. et al, Construction of New Amplifier Expression Vectors for High Levels of IL-2 Gene Expression. Int. J. Molecular Medicine 5:295–300, 2000, which is incorporated by reference herein. The HSP 70 promoter used was cut out from p173OR (Stressgen). The plasmid backbone containing the Kanamycin/neomycin resistance markers and a SV40 polyA site was cut out from pEGFP-1 (Clontech). The intron following the HIV 1 and HIV 2 promoters were taken from pCI-neo (Promega).The multiple cloning site and the BGH polyA was cut out from pcDNA3.1 (Invitrogen). These fragments were adapted using the KISS system (Tsang, T. C. et al, A Simple Method for Adapting DNA Fragments and PCR Products to All of the Commonly Used Restriction Sites. BioTechniques 20:51–52, 1996, which is incorporated herein by reference) to provide compatible overhangs to these fragments and therefore can be assembled into pHi&Hot-MCS and pHi&Hot-IL-2 using standard cloning protocols known in the art.

This pHi&Hot-MCS vector includes the features of an additional 1 kilobase space between the start of the hsp70 promoter and the other transcription units; a polyA site was placed behind the HIV2 LTR; a BGH polyA sequence was placed after the multiple cloning site, which would be used by the target DNA encoding a protein of interest; and one transcript provides both the Kanamycin and neomycin resistance genes.

The pHi&Hot-MCS vector contained in an *Echerichia coli* bacterial cell can be obtained as described hereinabove.

Example 6

A DNA sequence encoding IL-2 was engineered into the pHi&Hot-MCS vector so that the DNA sequence was under the transcriptional control of the HIV2 LTR. This vector was pHi&Hot-IL2 vector.

The resultant vector construct was transfected into mouse melanoma B 16 and Lewis Lung carcinoma (LL2) cells with a selecting medium containing neomycin. Parallel control experiments were also conducted using the control construct pHOT-IL-2 and pCMV IL-2. The transfected cells were then treated at 42° C. for 30 minutes and the level of IL-2 gene expression was assessed.

The results were that IL-2 expression increased 16 and 63-fold in the pHi&Hot-IL2 vector containing B16 and LL2 cells, respectively, compared to the cells containing the same vector held at 37° C. The level of expression was also 35 and 38 times greater than the control pHOT-IL-2 vector containing cells and 29 and 36-fold higher than the expression levels obtained from the pCMV-IL2 vector containing cells.

Example 7

Animal Studies pHi-Hot-IL-2 transfected mouse Lewis Lung carcinoma cells were injected into 2 groups of C57/B6 mice (Group D1 and Group D1*–4 mice in each group). Each mouse was subcutaneously injected with 500,000 pHi-Hot-IL-2-transfected mouse Lung carcinoma cells in the rear flank of the mouse. Beginning from 3 days after tumor cell injection, mice were placed in a tubular device and heat treated in a water bath. The device allowed the lower flank of each mouse to be immersed into the water. Group D1 was placed into water at 37° C. and Group D1* was placed into water at 42° C. Both groups were placed in a water bath for 30 minutes twice a week. Since the treatment was well tolerated, after day 11, all mice were then placed in water at 37° C. or 43° C. for 30 minutes every other day.

Tumor volume was measured prior to each heat treatment and the results represent the average tumor volume.

The results demonstrate in the mouse lung cancer model that those tumors treated with the pHi&Hot-IL2 vector at 42° C. resulted in tumor regression compared to those tumors with the pHi&Hot-IL2 vector at 37° C.

Example 8

Induction of gene expression by heat, gamma-radiation and chemotherapy

Materials and Methods

A. Vector construction

Three reporter constructs were made from pHOT-MCS (see results for further details). One construct contained beta-galactosidase (β-gal) as the reporter gene (from the pCMVB plasmid, Clontech, Palo Alto, Calif.) cloned into the Not I site of pHOT-MCS.

For the IL-2 construct, the human IL-2 gene (a gift from Dr. Evan Hersh, University of Arizona) was first adapted for EcoR1 site. Briefly, a 0.5 kb BamHI-PstI DNA fragment containing the IL-2 gene was inserted into the Sac-KiSS- (Tsang et al (1996) Biotechniques 20:51–53) following a complete digestion with BamHI and a partial digestion with PstI to create the plasmid pSac-KiSS-IL-2. The IL-2 gene was then excised from the pSac-KiSS-IL-2 as an EcoRI fragment and inserted into the EcoRI site of pHOT-MCS to generate pHOT-IL-2. The third reporter construct contained EGFP (Clontech, Palo Alto, Calif.) as a reporter gene, which was inserted into the Kpn I-Not I multiple cloning site of pHOT-MCS.

B. Cell Lines and Transfections

MCF-7, a human breast carcinoma cell line, was transfected with the pHOT-EGFP vector by standard calcium phosphate methodologies (Sambrook et al (1989) Molecular Cloning, A Laboratory Manual, Vol. 3, 16.32). Stable transfectants were obtained by selection with G418 (400 µg/ml) and were maintained in complete RPMI medium, (GIBCO, Gaithersburg, Md.) supplemented with 10% fetal bovine serum (JRH Biosciences, Lenaxa, Kans.). The cells were maintained at 37° C. in 5% $CO_2$.

For IL-2 studies, MCF-7 cells were seeded in 35 mm plates (Falcon, Franklin Lakes, N.J.) at $0.5 \times 10^6$ cells/plate. Cells were transfected with the plasmids using the lipid Novafector (VennNova, Pompano Beach, Fla.) at a ratio of 1 µg DNA to 4 µl of lipid for 6 hours. SW480, a human colon carcinoma cell line, was transfected using DMRIE-DOPE (Vical Inc, San Diego, Calif.) (Parker et al (1996) Cancer Gene Ther. 3:175–185).

For β-gal studies, SW480 cells were plated out at $4 \times 10^5$ cells/well in a six well tissue culture plate (Falcon, Franklin Lakes, N.J.). A lipid to DNA ratio of 4:1 was used for transfections. Transfections were performed in reduced serum media OPTI-MEM (GIBCO, Gaithersburg, Md.). Four hours after transfections, 0.5 ml of 30% FBS in OPTI-MEM was added to each well. The next day an additional 1 ml of 10% FBS in OPTI-MEM was added.

Forty-eight hours after transfection the cells were trypsinized and stained for β-gal using the Invitrogen β-gal staining kit (Invitrogen, Carlsbad, Calif.).

C. Cell Treatments

Transfected cells were plated overnight in a 35 mm² tissue culture dish (Falcon, Franklin Lakes, N.J.) at a density of 1×10⁶ cells in 5 ml of RPMI medium. The following day the cells were treated as follows. Heat shock treatment was performed by sealing the plate with parafilm and immersing it in a 42° C. water bath for 60 min. Geldanamycin (Sigma, St. Louis, Mo.) was added to the cell cultures at a concentration of 1 μg/ml. Gamma-radiation treatment was performed using a ⁶⁰Co gamma irradiation unit. The cells were exposed to a total of 3000 rads (225 rads/min) of radiation in a single dose. All treated cells were trypsinized and assayed by flow cytometry for EGFP expression at 4, 24, 48 and 72 hours post-treatment.

D. IL-2 Assay

Cell supernatants were harvested 24 hours after heat treatments. The supernatants were assayed by ELISA for IL-2 levels using MEDGENIX IL-2 EASIA Kit (Biosource Europa, Belgium).

E. Flow Cytometry

Flow cytometric analysis was performed using a FACStar$^{PLUS}$ flow cytometer (Becton Dickinson Immunocytometry Systems, Mountain View, Calif.). Data was acquired utilizing a COHERENT (Palo Alto, Calif.) 90-5 5 W argon ion water-cooled laser tuned to 488 nm at 100 mW power for excitation. Emitted fluorescence was collected with a standard 530/30 band pass filter. A minimum of 10,000 events were collected in a 'live' gate. Data was acquired and analyzed on an HP340 computer with Lysys II (Becton Dickinson Immunocytometry Systems Mountain View, Calif.) software. Data was collected as mean florescence channel of EGFP. An increase in 75 units of mean florescence channel indicates a doubling in fluorescence intensity (as per personal communications from Becton Dickinson, according to the formula:

$$\frac{\text{channel value}}{\text{channels per decade}} = 10^x$$

where x=log channel

Data is represented as the percent increase in EGFP intensity over background intensity.

F. Western Blots

Western immunoblots were performed to estimate production of heat shock proteins.

Cells to be assayed were washed with phosphate buffered saline and resuspended in cell lysis buffer. Total protein was estimated by the BCA protein assay (Pierce, Rockford, Ill.). Protein samples (30 mg each) were fractionated for Western blot analysis by separation on denaturing SDS-PAGE and transferred onto nitrocellulose filters. Filters were blocked by soaking the membrane in buffer containing 3% milk in TTBS (Tris-buffered saline containing 1% Tween-20) to minimize non-specific binding. After three washes in TTBS the membranes were incubated with anti-HSP 72/73 antibody (StressGen, Victoria, BC). Goat anti-mouse IgG-horse radish peroxidase (Pierce, Rockford, Ill.) was used as a secondary/developing antibody. Both incubations were performed at room temperature for 1 hour. The membrane was washed three times with TTBS and incubated in substrate reagent containing peroxide for 5 min. Heat shock proteins were detected by exposure to ELC hyperfilm and developed for autoradiogram. Heat shock protein expression was quantitated by scanning densitometry.

Results

A. Vector Construction

Figure 14:
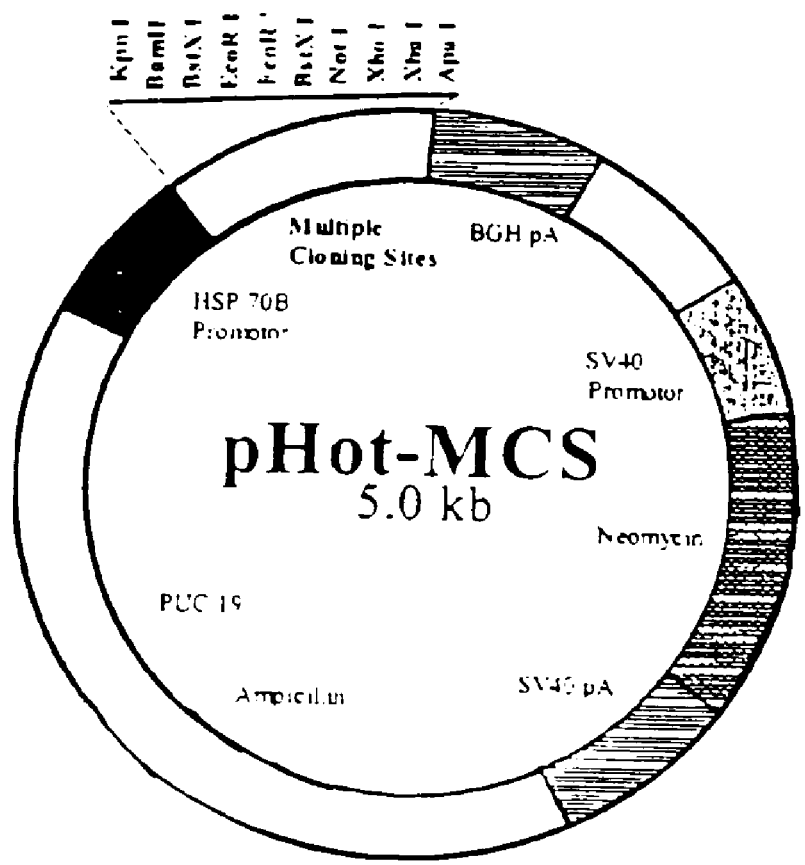
FIG. 14 Map of the HOT-MCS expression plasmid. The plasmid was generated by replacing the CMV promoter of the pcDNA3 expression plasmid with a 451 bp BamH1-HindIII fragment of the human HSP70B promoter derived from the p173OR plasmid.

The pHOT-MCS vector (FIG. 14) was generated by replacing the cytomegalovirus (CMV) promoter of pcDNA3 (Invitrogen, San Diego, Calif.) by a BamHI-HindIII fragment of the human HSP70B promoter from the p173OR plasmid (StressGen, Victoria, BC). The full-length HSP70B promoter is 2.3 kilo base pairs (kbp) in size, while the BamHI-HindIII fragment of the promoter is 451 bp in size. This adaptation resulted in a smaller vector, which was advantageous for further cloning. The pHOT-MCS vector also has a neomycin selectable marker that can be useful for in vitro research work. The pHOT-MCS vector has a large multiple cloning site to facilitate the cloning of genes into the vector. Thus, this newly constructed pHOT-MCS vector has many advantages over the p1730R plasmid (11.1 kbp).

B. Promoter Expression

The pHOT-MCS plasmid containing a beta-galactosidase reporter gene (pHOT-β-gal) was evaluated for its ability to be induced by heat shock treatment. SW480 cells were transfected with the plasmid by the lipofection technique as described in Materials and Methods. Twenty-four hours after transfection the cells were heated to 42° C. for one hour. Twenty-four hours after heat shock treatment the cells were stained for β-gal gene expression. The p 173OR plasmid expressing β-gal under the control of the full-length 2.3 kb HSP promoter was used as a positive control. SW480 human colon carcinoma cells were transfected with either the pHOT-β-gal or the p173OR expression plasmid using the lipid DMRIE/DOPE as described in Materials and Methods. Transiently transfected cells were exposed for 1 hour to either 37° C. or 42° C. as described. Forty-eight hours after transfection the cells were harvested and stained for β-gal using standard staining procedures (Invitrogen, San Diego, Calif.). Data are expressed as the percentage of cells staining positive for each treatment The analyses (Table 7) revealed that β-gal gene expression was not induced at 37° C., whereas the pHOT-β-gal plasmid transfected cells stained positive 24 hours after heat treatment. Results were comparable with both vectors. These results confirmed that the 451 bp BamHI/Hind III fragment of HSP70B promoter maintained it's ability to be induced by heat shock.

Table 7: Inducible Gene Expression by a Fragment of the Human HSP Promoter.

| PLASMID | Percent β-gal positive cells at: | |
|---|---|---|
| | 37° C. | 42° C. |
| p173OR | 0% | 27% |
| pHOT-β-gal | 0% | 23% |

Figure 15:
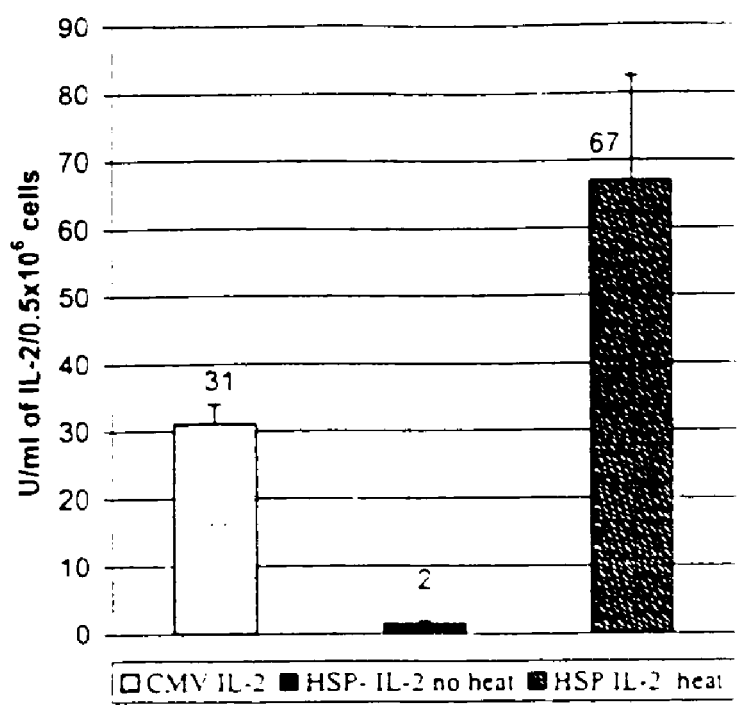
FIG. 15 Promoter strength comparison by IL-2 production. MCF-7 cells were plated overnight at a density of $0.5 \times 10^6$ cells per well in a six well plate. The cells were transfected with the pHOT-IL-2 plasmid using the lipid Novafector. The cells were heated to 42° C. for 60 min and returned to 37° C. Twenty-four hours later the supernatants were harvested and analyzed by ELISA for IL-2 levels. Results are the mean of triplicate experiments.

The promoter strength of the inducible expression vector was also tested against the CMV promoter. The IL-2 gene was cloned into the EcoRI site of the multiple cloning site of the pHOT-MCS vector. The pHOT-IL-2 plasmid and the pcDNA3-IL-2 plasmid were transfected into MCF-7 cells with the lipid Novafector. Twenty-four hours after transfection the cells were heated and 24 hours after heat treatment supernatants were collected and assayed for IL-2. Results (FIG. 15) showed that the pHOT-MCS vector promoter was twice as strong as the CMV promoter when induced by heat treatment (67 units v/s 31 units of IL-2).

C. Induction of the Transgene by Heat Shock, γ-Radiation and Geldanamycin

Due to the difficulty in quantitating and comparing β-gal assays and the expense of IL-2 assays, the enhanced green fluorescent protein (EGFP) reporter gene was cloned into the pHOT-MCS plasmid yielding the pHOT-EGFP plasmid. This plasmid can easily be detected by flow cytometry and was used for further experiments. MCF-7 cells were transfected with pHOT-EGFP by the calcium phosphate method and stable transfectants were selected and maintained with the antibiotic G418. Stable, as compared to transient, transfections were chosen in order to eliminate differences in transfection efficiencies between experiments thereby allowing direct comparisons of increases in gene expression.

Figure 16:
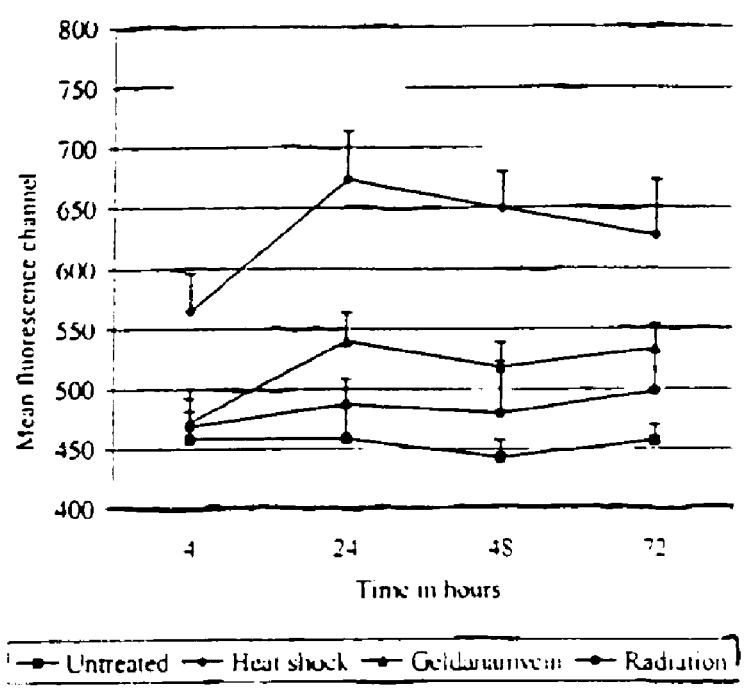
FIG. 16 Increase in EGFP expression. Mean fluorescence channel (MFC) of EGFP expression following treatment with heat, radiation or chemotherapy. MCF-7 cells were treated as described in Materials and Methods, harvested at the indicated time points and analyzed by flow cytometry for EGFP intensity.

Stably transfected MCF-7 cells were plated overnight into 35 mm, 6 well tissue culture plates at a density of $1 \times 10^6$ cells/plate. The next day, adherent cells were treated with either heat (42° C., 1 hour), γ-radiation (3000 rads, a previously determined optimal level) or geldanamycin (1 μg/ml). Synergy of gene induction was also analyzed for by using γ-radiation and geldanamycin treatments together. Four, 24, 48, and 72 hours after treatment, the cells were harvested and assayed for EGFP expression by flow cytometry. All transfected cells displayed a basal level of EGFP expression. Thus, results from the cell treatments are shown as the mean florescence channel (FIG. 16) and as the percent increase in EGFP intensity (Table 8) over the basal level. Flow cytometric analyses indicated that heat shock treatment induced the highest level of gene expression. As early as 4 hours post-treatment, there was a 243% increase in EGFP expression above the basal level. Maximal EGFP expression was observed at 24 hours after heat treatment (387% increase above background) after which it started to decline. Geldanamycin was also observed to induce the HSP promoter, with EGFP intensity increasing to 208% above background at 24 hours post-treatment. Gamma-radiation also induced the HSP promoter, although to a weaker extent than geldanamycin treatment. The highest level of gene expression was seen at 48 hours post-radiation treatment, with an increase of 150% over background levels. Finally, a combination of geldanamycin and radiation treatments together was not observed to increase gene expression (i.e. act synergistically) above that seen with either treatment alone (data not shown). These results were significant in that it demonstrated that the pHOT-EGFP vector could be induced not only by heat shock, but also by γ-radiation and chemotherapy.

Table 8: Percent Increase in EGFP Intensity. Mean Fluorescence Channel units from FIG. 16 were converted into percent intensity increases above background. An increase in 75 units of MFC=a doubling in intensity. The above formula was used to calculate the percent increase in EGFP intensity over background, which was considered to be 100%.

|  | 4 hours | 24 hours | 48 hours | 72 hours |
|---|---|---|---|---|
| Heat | 243 | 387 | 376 | 327 |
| Geldanamycin | 120 | 208 | 201 | 201 |
| Radiation | 113 | 138 | 150 | 154 |

D. Analysis of Heat Shock Proteins by Western Blots

Figure 17:
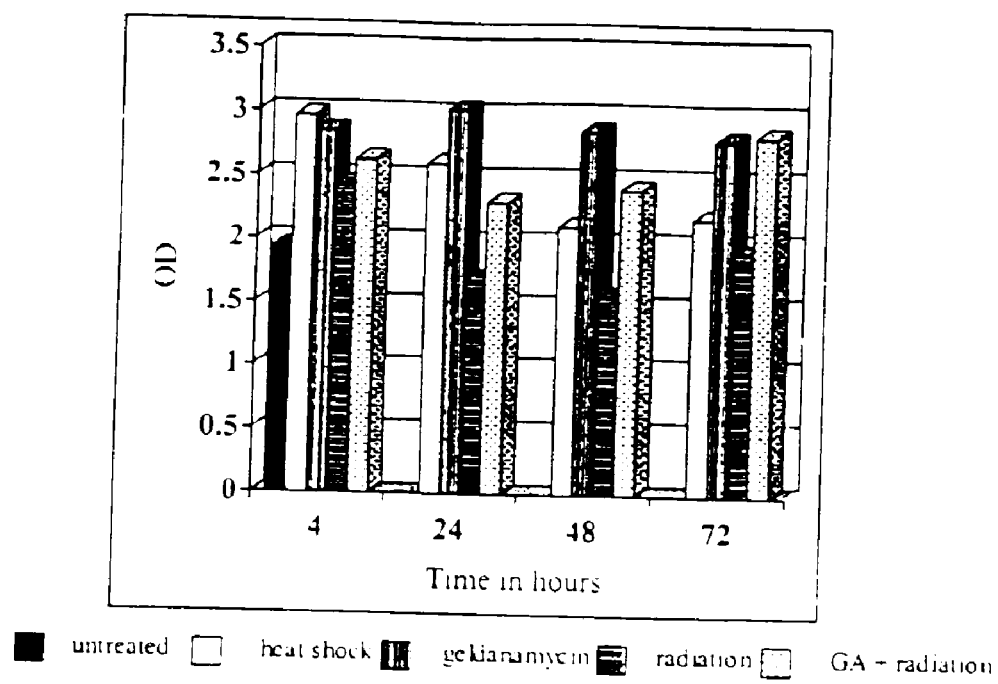
FIG. 17 HSP72/72 protein expression after treatment with either heat, radiation or chemotherapy. MCF-7 cells were treated as described in FIG. 2 and heat shock protein expression quantitated by western blotting and densitometry at the indicated time points. Data are presented optical density for each measurement.

As the time course for induction of EGFP expression by both geldanamycin and γ-radiation treatments were different from that of heat-shock treatment, Western blots were performed on the treated cells at these time points to quantitate HSP72/73 production. As each of the treatments theoretically induced EGFP expression via the HSP promoter, the treatments should have induced an increase in cellular heat shock proteins. Western blot analyses (FIG. 17) for HSP72/73 expression indicated that all three treatments (heat, radiation and geldanamycin) induced the HSP 72/73 proteins. The highest level of HSP 72/73 production was induced by heat at 4 hours post-treatment. However, at 24 hours post-treatment and thereafter, treatment with geldanamycin induced higher levels of HSP72/73 expression. Gamma-radiation also induced HSP72/73 protein expression at 4 hours post-treatment, but the levels were not significant at the later timepoints.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying, out the invention which are obvious to those skilled in the art are intended to be within the scope of the following claims.

What is claimed is:

1. A method of expressing a selected polynucleotide of interest in a mammalian cell which comprises a recombinant DNA, the method comprising subjecting the mammalian cell to heated conditions and at least one of a treatment selected from the group consisting of radiation, chemotherapy, and immunotherapy, for a time suitable to activate expression of the polynucleotide of interest; wherein said recombinant DNA comprises a heat shock promoter operably linked to a DNA sequence encoding a transactivating protein, and a second promoter operably linked to the selected polynucleotide of interest, wherein the second promoter is activated by the transactivating protein.

2. The method of claim 1, wherein said second promoter is an HIV-1 promoter or an HIV-2 promoter.

3. The method of claim 1, wherein said transactivating protein is HIV tat protein.

4. The method of claim 1, wherein the heat shock promoter is selected from the group consisting of a HSP70 promoter, a HSP90 promoter, a HSP60 promoter, a HSP25 promoter, a ubiquitin promoter, and a HSP28 promoter.

5. The method of claim 1, wherein the heat shock promoter is a HSP70 promoter or a HSP70B promoter.

6. The method of claim 1, wherein the treatment is radiation.

7. The method of claim 6, wherein the radiation is γ-radiation.

8. The method of claim 1, wherein the treatment is chemotherapy.

9. The method of claim 8, wherein the chemotherapy comprises contacting the cell with one or more chemotherapeutic agents selected from the group consisting of adriamycin, 5-fluorouracil, etoposide, camptothecin, actinomycin-D, mitomycin C, cisplatin, geldanamycin, and hydrogen peroxide.

10. The method of claim 1, wherein the heated conditions comprise heating to a temperature of 37° C. to 42° C.

11. The method of claim 1, wherein the heated conditions comprise heating to a temperature of 38° C. to 41° C.

12. The method of claim 1, wherein the selected polynucleotide encodes a polypeptide, protein, ribozyme, or an antisense molecule.

13. The method of claim 12, wherein the selected polynucleotide encodes a polypeptide.

14. The method of claim 13, wherein the polypeptide is selected from the group consisting omithine decarboxylase antizyme protein, p53, p16, neu, IL1, IL2, IL4, IL7, IL12, IL15, FLT-3 ligand, GM-CSF, G-CSF, IFNγ, IFNα, TNF, HSV-TK, I-CAM1, HLA-B7 and TIMP-3.

15. The method of claim 1, wherein said recombinant DNA further comprises a gene encoding a selectable marker.

16. The method of claim 1, wherein said mammalian cell is a cancer cell.

17. The method of claim 16, wherein said cancer cell is a cell selected from the group consisting of a brain cell, a lung cell, a liver cell, a bladder cell, a spleen cell, a kidney cell, a lymph node cell, a small intestine cell, a pancreatic cell, a blood cell, a colon cell, a stomach cell, a breast cell, a endometrial cell, a prostrate cell, a testicular cell, a ovarian cell, a skin cell, a vulval cell, a cervical cell, an esophageal cell, a bone marrow cell, a neuronal cell, and a muscle cell.

18. The method of claim 1, which is performed in vitro.

19. The method of claim 1, which is performed in vivo.

20. The method of claim 19, wherein said cell is in a mammal.

21. The method of claim 20, wherein said mammal is a human.

22. The method of claim 20, wherein the expression of the selected polynucleotide provides a therapeutic benefit to the mammal.

23. The method of claim 20, wherein the expression of the selected polynucleotide provokes an immune response in the mammal.

* * * * *